(12) United States Patent
Thorson

(10) Patent No.: US 6,884,604 B2
(45) Date of Patent: Apr. 26, 2005

(54) GLYCORANDOMIZATION AND THE PRODUCTION OF NOVEL ERYTHRONOLIDE AND COUMARIN ANALOGS

(75) Inventor: Jon S. Thorson, Madison, WI (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 79 days.

(21) Appl. No.: 10/109,672

(22) Filed: Apr. 1, 2002

(65) Prior Publication Data

US 2003/0068669 A1 Apr. 10, 2003

Related U.S. Application Data

(60) Provisional application No. 60/279,682, filed on Mar. 30, 2001.

(51) Int. Cl.$^7$ ............................ C12P 19/18; C12P 19/30
(52) U.S. Cl. ............................ 435/89; 435/97; 435/76; 435/72; 435/74; 435/75
(58) Field of Search ............................ 435/97, 89, 76, 435/72, 74, 75

(56) References Cited

U.S. PATENT DOCUMENTS 5,998,194 A * 12/1999 Summers et al. ...... 435/252.33
2003/0055235 A1 * 3/2003 Thorson et al. ............ 536/23.2

FOREIGN PATENT DOCUMENTS

| WO | WO 99/31224 | * | 6/1999 |
| WO | WO 02/48331 | | 6/2002 |

OTHER PUBLICATIONS

Stauoton et al., "Biosynthesis of Erythromycin and Rapamycin", Chem. Rev., 1997, 97:2611–2629.
Steffensky et al., "Identification of the Novobiocin Biosynthetic Gene Cluster of Streptomyces spheroides NCIB", Antimicrob. Agents Chemotherap., 2000, 44:1214–1222.
Summers et al. "Sequencing and mutagenesis of genes from the erythromycin biosynthetic gene cluster of Saccaropolyspora erythraea that are involved in L–mycarose and D–desosamine production", Microbiol., 1997, 143:3251–3262.
Thompson et al., "Synthesis of Vancomycin from the Aglycon", J. Am. Chem. Soc., 1999, 121:1237–1244.
Thorson et al. "Nature's Carbohydrate Chemists: The Enzymatic Glycosylation of Bioactive Bacterial Metabolties", Curr. Org. Chem., 2001, 5:139–167.
Thorson et al., "Enediyne Biosynthesis and Self Resistance: A Progress Report," Biorgan. Chem., 1999, 27:172–188.
Thorson et al., "Understanding and Exploiting Nature's Chemical Arsenal: The Past, Present and Future of Calicheamicin Research," Curr. Pharm. Des., 2000, 6:1841–1879.

Tsai et al., "The high–resolution crystal structure of a 24–kDa gyrase B fragment from E. coli complexed with one of the most potent coumarin inhibitors, clorobiocin" Proteins, 1997, 28:41–52.
Verdier et al., "Lincomycin and clindamycin conformations. A fragment shared by macrolides, ketolides and lincosamides determined from TRNOE ribsomoe–bound conformations", Biorgan. & Med. Chem., 2000, 8:1225–1243.
Volchegursky et al., "Biosynthesis of the Anti–Parasitic Agent Megalomicin: Transformation of Erythromycin to Megalomicin in Saccharopolyspora erythraea", Mol. Microbiol., 2000, 37:752–762.
Weymouth–Wilson, "The Role of Carbohydrates in Biologically Active Natural Products," Nat. Prod. Rep., 1997, 14:99–110.
Goldman et al., "Inhibition of transglycosylation involved in bacterial peptidoglycan synthesis", Curr. Med. Chem., 2000, 7:801–820.
Goossens et al., "Cellular Uptake and Interaction with Purified Membranes of Rebeccamycin Derivatives", Eur. J. Pharmacol., 2000, 389:141–146.
Hansen et al., "Altromycin B Threads the DNA Helix Interacting with Both the Major and Minor Grooves to Position Itself for Site–Directed Alkylation of Guanine N7", J. Am. Chem. Soc., 1995, 117:2421–2429.
Hutchinson, "Combinatorial Biosynthesis for New Drug Discovery", Curr. Opin. Microbiol., 1998, 1:319–329.
Jiang et al., "A General Enzymatic Method for the Synthesis of Natural and 'Unnatural' UDP– and TDP–Nucleotide Sugars", Journal of the Am. Chem. Soc., 2000, 122(28):6803–6804.
Jiang et al., "Expanding the Pyrimidine Diphosphosugar Repertoire: The Chemoenzymatic Synthesis of Amino– and Acetamidoglucopyranosyl Derivatives", Angrew Chem. Int. Engl., 2001, 40(8):1502–1505.
Johnson et al., "Mechanisms and Pathways from Recent Deoxysugar Biosynthesis Research", Curr. Opin. Chem. Biol., 1998, 2:642–649.

(Continued)

Primary Examiner—Francisco Prats
(74) Attorney, Agent, or Firm—Godfrey & Kahn, S.C.

(57) ABSTRACT

The present invention provides combinatorial methods for rapidly generating a diverse library of glycorandomized structures, comprising incubating one or more aglycons and a pool of NDP-sugars in the presence of a glycosyltransferase. The glycosyltransferase may be one that is associated with or involved in production of natural secondary metabolites, or one which is putatively associated with or involved in production of natural secondary metabolites. The glycosyltransferase may show significant flexibility with respect to its NDP-sugar donors and/or its aglycons. NDP-sugar donors may be commercially available, or may be produced by utilizing mutant or wild type nucleotidyltransferases significant flexibility with respect to their substrates.

24 Claims, 5 Drawing Sheets

OTHER PUBLICATIONS

Kampranis et al., "Probing the Binding of Coumarins and Cyclothialidines to DNA Gyrase", *Biochem.*, 1999, 28:1967–1976.

Keniry et al., "The Three–Dimensional Structure of the 4:1 Mithramycin:d (ACCCGGGT)2 Complex: Evidence for an Interaction between the E Saccharides", *Biopolymers*, 2000, 54:104–114.

Kirschning et al., "Chemical and Biochemical Aspects of Deoxysugars and Deoxysugar Oligosaccharides", *Top Curr. Chem.*, 1997, 188:1–84.

Kurihara et al., Cladinose Analogues of Sixteen–Membered Macrolide Antibiotics. I. Synthesis of 4–O–Alkyl–L–cladinose Analogues via Glycosylation, *J. Antiobiot.*, 1996, 49:582–592.

Laurin et al., "Synthesis and in vitro evaluation of novel highly potent coumarin inhibitors of gyrase B", *Biorgan. & Med. Chem. Lett.*, 1999, 9:2079–2084.

Lewis et al., "The nature of inhibition of DNA gyrase by the courmarins and the cyclothialidines revealed by X–ray crystallography", *EMBO J.*, 1996, 15:1412–1420.

Lindquist et al., "Purification, Characterization and HPLC Assay of Salmonella Glucose–1–phosphate Thymidylytransferase from the Cloned rfbA Gene", 1993, 211:763–770.

Liu et al. "Pathways and Mechanisms in the Biogenesis of Novel Deoxysugars by Bacteria" *Annu. Rev. Microbiol.*, 1994, 48:223–256.

Marcu, "Novobiocin and related coumarins and depletion of heat shock protein 90–dependent signaling proteins",*J. Nat. Cancer Inst.*, 2000, 92:242–248.

McNicholas et al., "Evernimicin Binds Exclusively to the 50S Ribosomal Subunit and Inhibits Translation in Cell–Free Systems Derived from both Gram–Positive and Gram–Negative Bacteria", *Antimicrob. Agents & Chemotherapy*, 2000, 44:1121–1126.

Myers et al., "A Compariosn of DNA Cleavage by Neocarzinostatin Chromophore and Its Aglycon: Evaluating the Role of the Carbohydrate Residue", *J. Am. Chem. Soc.*, 1997, 119:2965–2972.

Pavlopoulos et al., "Characterization of the Sequential Noncovalent and Covalent Interactions of the Antitumor Antibiotic Hedamycin with Double Stranded DNA by NMR Spectroscopy", *J. Mol. Recognition*, 1999, 12:346–354.

Pavlopoulos et al., "Structural Characterization of the 1:1 Adduct Formed between the Antitumor Antibiotic Hedamycin and the Oligonucleotide Duplex d(CACGTG)2 by 2D NMR Spectroscopy",*Biochem.*, 1996, 35:9314–9324.

Potier, La nature: une bonne source de nouveaux produits utiles à la santé des hommes, des animaux et des végétaux . . . pour longetmps encore!, *Actual. Chim.* 1999, 11:9–11 (including English summary).

Prudhomme, "Indolocarbazoles as Anti–cancer agents", *Curr. Pharm. Des.*, 1997, 3:265–290.

Qu et al., "A DNA Binding Indolocarbazole Disaccharide Derivative Remains Highly Cytotoxic without Inhibiting Topoisomerase I", *Anti–Cancer Drug Des.*, 1999, 14:433–442.

Sinnott, "Catalytic Mechanisms of Enzymic Glycosyl Transfer", *Chem. Rev.*, 1990, 90:1171–1202.

Solenberg et al.,"Production of Hybrid Glycopeptide Antibiotics in vitro and in *Streptomyces toyocaensis*", *Chem. Biol.*, 1997, 4:195–202.

Stassinopoulos et al., "Solution Structure of a Two–Base DNA Bulge Complexed with an Enediyne Cleaving Analog", *Science*, 1996, 272:1943–1946.

Abu–salah, "Amphotericin B: an update", *Brit. J. Miomed. Sci.*, 1996, 53:122–133.

Bailly et al., "Recognition of Specific Sequences in DNA by a Topoisomerase I Inhibitor Derived from the Antitumor Drug Rebeccamycin", *Mol. Pharmacol.*, 1998, 53:77–87.

Bailly et al., "Enhanced Binding to DNA and Topoisomerase I Inhibition by an Analog of the Antitumor Antibiotic Rebeccamycin Containing an Amino Sugar Residue", *Mol. Pharmacol.*, 1999, 55:377–385.

Barton et al., "Expanding pyrimidine diphosphosugar libraries via structure–based nucleotidylytransferase engineering", PNAS, 2002, 99:13397–13402.

Barton et al., "Structure, mechanism and engineering of a Nucleotidylytransferase as a first step toward glycorandomization", *Nat. Struct. Biol.*, 2001, 8(6):545–551.

Bertho et al., "Transferred Nuclear Overhauser Effect Study of Macrolide–Ribosome Interactions: Correlation between Antibiotic Activities and Bound Conformations", *Biorg. & Med. Chem.*, 1998, 6:209–221.

Bertho et al., "Solution Conformation of Methylated Macrolide Antibiotics Roxithromycin Using NMR and Molecular Modeling, Ribosome–bound Conformation Determined by TRNOE and Formation of Cytochrome P450–methbolite Complex",*Internatl. J. Biol. Macromol.*, 1998, 22:103–127.

Bertho et al., "Conformational Analysis of Ketolide, Conformations of RU 004 in Solution and Bound to Bacterial Ribosomes"*J. Med. Chem.*, 1998, 41:3373–3386.

Ferroud et al., "Synthesis and biological evaluation of coumarincarboxylic acids as inhibitors of gyrase B. 1–rhamnose as an effective substitute for 1–noviose", *Biorgan. & Med. Chem. Lett.*, 1999, 9:2881–2886.

Fish et al., "Structure–Activity Studies of Tylosin–related Macrolides",*J. Antibiol.*, 1996, 49:1044–1048.

Ge et al., "Vancomycin Derivatives that Inhibit Peptidoglycan Biosynthesis without Binding D–Ala–D–Ala", *Science*, 1999, 284:507–511.

Ge et al., "Reconstruction of Vancomycin by Chemical Glycosylation of the Pseudoaglycon", *J. Am. Chem. Soc.*, 1998, 120:11014–11015.

Georgopapadakou, "Antifungals: Mechanism of Action and Resistance, Established and Novel Drugs",*Curr. Opin. Microbiol.*, 1998, 1:547–557.

Gharbi–Benarous et al., "Confirmational analysis of josamycin, a 16–membered macrolide free in solution and bound to bacterial ribosomes",*J. Chem. Soc. Per. Trans. II*, 1999, pp. 529–543.

\* cited by examiner

GLYCORANDOMIZATION AND THE PRODUCTION OF NOVEL ERYTHRONOLIDE AND COUMARIN ANALOGS

PRIORITY

The present application claims priority to U.S. Provisional Patent Application No. 60/279,682, filed Jun. 30, 2000 which is also incorporated herein in its entirety.

GOVERNMENT SUPPORT

This work was supported in part by grants from the National Cancer Institute (NCI Core Grant 08748). The Government may have certain rights in this invention.

FIELD OF THE INVENTION

The present invention is directed to glycosyltransferases and methods for their use. The present invention is also directed to methods of synthesizing novel glycosylated compounds.

BACKGROUND

A recent estimate suggests roughly 70% of current lead compounds in modern drug discovery derive directly from the natural products, many of which are glycosylated bacterial metabolites. Potier, P. *Actual. Chim.* 11: 9 (1999). Thus, bacterial glycosyltransferases and their corresponding sugar substrates contribute significantly to the diversity of pharmaceutically important metabolites. A glycosylated metabolite is one that is comprised of both a central core structure (often called the "aglycon") and various sugar (or "glycosyl") attachments.

Carbohydrates are able to exhibit target specificity and often the affinity of carbohydrate ligands for their target are defined by the structure and length of the sugar chain carried by the aglycon. Traditionally, carbohydrate ligands of bioactive agents have been implicated in the control of drug pharmacokinetics such as absorption, distribution, metabolism and/or excretion. However, recent growing evidence has led to a change in this dogmatic view.

Pyran (or furan) ring rigidity in conjunction with glycosidic bond flexibility lends itself to preorganization while deoxygenated and/or functionalized sugars also provide unusual hydrophobic and hydrophilic domains. Furthermore, there exist many examples in which removal of these critical ligands leaves barren aglycons with little or no biological activity. Thus, carbohydrates provide great functional diversity to secondary metabolite activity. Thorson, J. S. et al. "Nature's Carbohydrate Chemists: The Enzymatic Glycosylation of Bioactive Bacterial Metabolites," *Curr. Org. Chem.* 5: 139–167 (2001); Weymouth-Wilson, A. C. "The Role of Carbohydrates in Biologically Active Natural Products," *Nat. Prod. Rep.* 14: 99–110 (1997).

Carbohydrate ligands often determine the specificity and affinity with which bioactive metabolites bind to DNA. One of the best characterized glycoconjugates is calicheamicin $\gamma_1^I$ (FIG. 1, 1), a member of the enediyne family of antitumor antibiotics isolated from *Micromonospora echinospora*. Thorson, J. S. et al "Enediyne Biosynthesis and Self Resistance: A Progress Report," *Bioorgan. Chem.* 27: 172–188 (1999) and references therein; Thorson, J. S. et al. "Understanding and Exploiting Nature's Chemical Arsenal: The Past, Present and Future of Calicheamicin Research," *Curr. Pharm. Des.* 6: 1841–1879 (2000) and references therein. The aryltetrasaccharide of calicheamicin defines both the DNA binding specificity and the high affinity (estimated to be $10^6-10^8$) of calicheamicin.

In the related enediyne neocarzinostatin (FIG. 1, 2), the carbohydrate ligand is 2,6-dideoxy-2-methylamino-α-D-galacto-hexopyranose (2-N-methyl-α-D-fucosamine) and, in contrast to most minor groove-binding aminoglycosyl ligands, the neocarzinostatin pyranose acts as an anchor, through numerous intermolecular contacts, and defines how deep neocarzinostatin can penetrate the major groove. This locks the molecule into position and thus, ultimately defines the specific sites of DNA-cleavage as well as enhances (possibly as an internal base) the efficiency of cleavage. Stassinopoulos, A. et al. "Solution Structure of a Two-Base DNA Bulge Complexed with an Enediyne Cleaving Analog," *Science* 272: 1943–1946 (1996); Myers, A. G. et al. "A Comparison of DNA Cleavage by Neocarzinostatin Chromophore and Its Aglycon: Evaluating the Role of the Carbohydrate Residue," *J. Am. Chem. Soc.* 119: 2965–2972 (1997).

Like the sugar ligands of calicheamicin $\gamma_1^I$ and neocarzinostatin, the carbohydrate ligands of anthracyclines (e.g. daunorubicin, 5, among the most potent and widely used anticancer agents) are known to contribute directly to DNA binding, via intermolecular contacts, and to retard the activity of polymerases in some cases. Also, a direct correlation between increased glycosylation and lower toxicity has been demonstrated. Kirschning, A. et al. "Chemical and Biochemical Aspects of Dexoysugars and Deoxysugar Oligosaccharides," *Top. Curr. Chem.* 188: 1–84 (1997). Similar roles for the carbohydrates in DNA minor groove binding of the pluramycin antitumor antibiotics (e.g. altromycin B, a DNA alkylator, FIG. 1, 3), the antimicrobial aureolic acids (e.g. chromomycin $A_3$, an inhibitor of replication/translation, FIG. 1, 8), and various other angucyclines, have been observed. Hansen, M. et al. "Threads the DNA Helix Interacting with Both the Major and Minor Grooves to Position Itself for Site-Directed Alkylation of Guanine N7," *J. Am. Chem. Soc.* 117: 2421–2429 (1995); Pavlopoulos, S. et al. "Structural Characterization of the 1:1 Adduct Formed between the Antitumor Antibiotic Hedamycin and the Oligonucleotide Duplex d(CACGTG)2 by 2D NMR Spectroscopy." *Biochem.* 35: 9314–9324 (1996); Pavlopoulos, S. et al. "Characterization of the Sequential Non-covalent and Covalent Interactions of the Antitumor Antibiotic Hedamycin with Double Stranded DNA by NMR Spectroscopy," *J. Mol. Recognition* 12: 346–354 (1999); Johnson, D. A. et al. "Mechanisms and Pathways from Recent Deoxysugar Biosynthesis Research," *Curr. Opin. Chem. Biol.* 2: 642–649 (1998); Keniry, M. A. et al "The Three-Dimensional Structure of the 4:1 Mithramycin:d(ACCCGGGT)2 Complex: Evidence for an Interaction between the E Saccharides," *Biopolymers* 54: 104–114 (2000).

Saccharides of secondary metabolites are also responsible for interaction with RNA. Examples include the orthosomycins such as the antibiotic evernimicin (FIG. 1, 11), which specifically binds to the 50S ribosomal subunits of *E. coli* and *S. aureus* and ultimately inhibits protein synthesis. McNicholas, P. M. et al "Evernimicin Binds Exclusively to the 50S Ribosomal Subunit and Inhibits Translation in Cell-Free Systems Derived from both Gram-Positive and Gram-Negative Bacteria," *Antimicrob. Agents & Chemotherapy* 44: 1121–1126 (2000).

Other examples include the macrolides (described further herein), such as erythromycin D (FIG. 2b, 18), which generally inhibit protein synthesis by inhibiting the 50S ribosome via carbohydrate ligand-mediated binding with the 23S ribosomal subunit and various proteins. Fish, S. A. et al. "Structure-Activity Studies of Tylosin-related Macrolides," *J. Antibiot.* 49: 1044–1048 (1996). Extensive work has established the critical importance of the macrolide carbohydrate ligands in bioactivity. Kurihara, K. et al. "Analogues of Sixteen-Membered Macrolide Antibiotics. I. Synthesis of 4-O-Alkyl-L-cladinose Analogues via Glycosylation," *J. Antibiot.* 49: 582–592 (1996). Likewise, the classical aminoglycosides, (e.g. streptomycin, FIG. 1, 6) interact with the small (30S) subunit of eubacteria-type ribosomes which generally leads to translational misreading.

Carbohydrate ligands also play a role in metabolites which interact with cell walls/membranes. For example, the non-ribosomal peptide antibiotic vancomycin (FIG. 1, 7) kills cells by binding to the N-acyl-D-Ala-D-Ala termini of uncrosslinked lipid-PP-disaccharide-pentapeptides. Goldman, R. C. et al., *Curr. Med. Chem.* 7: 801 (2000). While it is known that the carbohydrate portion of vancomycin is not directly involved in this binding event, deglycosylation or N-alkylation of the terminal vancosamine sugar of vancomycin shows remarkably different antibacterial profiles, while analogs with synthetically modified carbohydrates were found to operate via a mechanism distinct from that of vancomycin. Solenberg, P. J. et al. "Production of Hybrid Glycopeptide Antibiotics in vitro and in *Streptomyces toyocaensis,*" *Chem. Biol.* 4: 195–202 (1997); Ge, M. et al. "Reconstruction of Vancomycin by Chemical Glycosylation of the Pseudoaglycon," *J. Am. Chem. Soc.* 120: 11014–11015 (1998); Thompson, C. et al "Synthesis of Vancomycin from the Aglycon," *J. Am. Chem. Soc.* 121: 1237 (1999); Ge, M. et al. "Vancomycin Derivatives that Inhibit Peptidoglycan Biosynthesis without Binding D-Ala-D-Ala," *Science* 284: 507–511(1999).

As another example, the polyenes, such as amphotericin B (FIG. 1, 9), bind selectively to ergosterol in the cell membrane of susceptible fungi, inducing changes in permeability that ultimately lead to cell death. Georgopapadakou, N. H., "Antifungals: Mechanism of Action and Resistance, Established and Novel Drugs," *Curr. Opin. Microbiol.* 1: 547–557 (1998); Abusalah, K. M., *Brit. J. Biomed. Sci.* 53: 122 (1996). In the amphotericin B-cholesterol aggregate cylindrical complex in the plasma membrane, critical hydrogen-bonding contacts between the polyene sugar and sterol contribute specificity for ergosterol over cholesterol.

Carbohydrate ligands often influence or determine interactions between bioactive metabolites and proteins. In this regard, the indolocarbazoles are an interesting class of metabolite. Prudhomme, M., *Curr. Pharm. Des.* 3: 265 (1997); Qu, X. G. et al. "A DNA Binding Indolocarbazole Disaccharide Derivative Remains Highly Cytotoxic without Inhibiting Topoisomerase I," *Anti-Cancer Drug Des.* 14: 433–442 (1999); Bailly, C. et al. "Enhanced Binding to DNA and Topoisomerase I Inhibition by an Analog of the Antitumor Antibiotic Rebeccamycin Containing an Amino Sugar Residue," *Mol. Pharmacol.* 55: 377–385 (1999); Bailly, C. et al. "Recognition of Specific Sequences in DNA by a Topoisomerase I Inhibitor Derived from the Antitumor Drug Rebeccamycin," *Mol. Pharmacol.* 53: 77–87 (1998); Goossens, J. F. et al. "Cellular Uptake and Interaction with Purified Membranes of Rebeccamycin Derivatives," *Eur. J. Pharmacol.* 389: 141–146 (2000). The indolocarbazoles, can be subdivided into two subgroups depending on the nature of the linkage between the carbohydrate residue and the heterocyclic chromophore. Compounds with the sugar attached to the two indole nitrogens (e.g. staurosporine, FIG. 1, 12) have little or no interaction with nucleic acids but strongly inhibit different protein kinases. In contrast, the second subgroup consists of indolocarbazole derivatives in which the carbohydrate moiety is attached to only one indole nitrogen, (e.g. rebeccamycin, 10) which does not inhibit PKC but instead its activity is attributed to the ability to induce topoisomerase-I-dependent DNA-strand breaks. These incredibly different activities attest to the critical role of the saccharide ligand.

As another example, novobiocin (FIG. 1, 4, discussed further herein) is a naturally-occurring coumarin which targets DNA gyrase, the bacterial type II topoisomerase which can introduce negative supercoils into DNA using the free energy of ATP hydrolysis. Structural analyses reveal a significant overlap of the novobiocin sugar constituent and the binding site of the ATP adenine ring. Kampranis, S. C. et al. "Probing the Binding of Coumarins and Cyclothialidines to DNA Gyrase," *Biochem.* 28: 1967–1976 (1999).

Macrolide antibiotics and coumarin antibiotics are clinically important examples of biologically active glycosylated secondary metabolites. The macrolides are a critical group of compounds due to their potent activity against Gram-positive bacteria. These compounds are generally classified by ring size of the aglycon lactone which contains either 12, 14, or 16 residues. Of these, the 14-membered ring and 16-membered ring families have been extensively studied from which erythromycin $A_1$, oleandromycin, spiramycin, josamycin and midecamycin are used clinically. In general, these metabolites inhibit protein synthesis by inhibiting the 50S ribosome via specific binding with the 23S ribosomal subunit and various proteins. Fish, S. A. et al. (1996).

The 16-member macrolides are generally found to bind 23S rRNA and inhibit peptidyltransferase activity while the 14-member macrolides generally inhibit the translocation of peptidyl-tRNA. Extensive work has established the critical importance of the carbohydrate ligands in bioactivity. Weymouth-Wilson, A. C. (1997); Kurihara, K. et al. (1996); Bertho, G. et al. "Conformational Analysis of Ketolide, Conformations of RU 004 in Solution and Bound to Bacterial Ribosomes," *J. Med. Chem.* 41: 3373–3386 (1998); Bertho, G. et al. "Solution Conformation of Methylated Macrolide Antibiotics Roxithromycin and Erythromycin Using NMR and Molecular Modeling. Ribosome-bound Conformation Determined by TRNOE and Formation of Cytochrome P450-metbolite Complex," *Internatl. J. Biol. Macromol.* 22: 103–127 (1998); Bertho, G. et al. "Transferred Nuclear Overhauser Effect Study of Macrolide-Ribosome Interactions: Correlation between Antibiotic Activities and Bound Conformations," *Biorg. & Med. Chem.* 6: 209–221 (1998); Gharbi-Benarous, J. et al. *J. Chem. Soc. Per. Trans. II* 529 (1999); Verdier, L. et al. *Biorgan. & Med. Chem.* 8: 1225 (2000).

Katz and coworkers have demonstrated the biosynthesis of the megalomicins (e.g. FIG. 2, 19) proceeds from erythronolide B (16) in a stepwise manner (FIG. 2*b*) and interestingly, the conversion of erythromycin D (18) to megalomycin A (19), via oxidation and the addition of a single sugar 2,3,4,6-tetradeoxy-3-dimethylamino-β-D-threo-hexopyranose (megosamine), changes the molecule's activity from an antibiotic (erythromycin D) to an antiparasitic/antiviral agent (megalomycin A). Volchegursky, Y. et al. "Biosynthesis of the Anti-Parasitic Agent Megalomicin: Transformation of Erythromycin to Megalomicin in *Saccharopolyspora erythraea,*" *Mol. Microbiol.* 37: 752–762 (2000).

Novobiocin (FIG. 1, 4) is a naturally-occurring coumarin from *Streptomyces spheroides* which targets DNA gyrase.

DNA gyrase from *E. coli* is an $A_2B_2$ complex in which each polypeptide displays distinct functional domains and the coumarins specifically inhibit the ATPase reaction of GyrB in a competitive manner. The complexes of the 24 kDa GyrB fragment with novobiocin and a related coumarin, chlorbiocin, show the binding sites for ATP and coumarins partially overlap. Tsai, F. T. F et al. *Proteins* 28: 41 (1997); Lewis, R. J. et al. *EMBO J.* 15: 1412 (1996). In particular, these high resolution structures reveal a significant overlap of the drug sugar constituent (3-O-aminocarbonyl)-6-deoxy-5-C-methyl-4-O-methyl-β-D-lyxo-hexopyranose, also known as β-D-noviose, in novobiocin) and the binding site of the ATP adenine ring with specific sugar-protein hydrogen-bonding interactions between the sugar C-2 and Asn 46, the sugar C-3 amide carbonyl with Thr 165 and amine with Asp 73/Val 43 main chain atoms. Site directed mutagenesis of these GyrB amino acids supports the structural assignments. Kampranis, S. C. et al. *Biochem.* 28: 1967 (1999). Interestingly, while these interactions are critical, the replacement of D-noviose with L-rhamnose has recently provided analogs with similar activity and potency. Ferroud, D. et al. *Biorgan. & Med. Chem. Lett.* 9: 2881 (1999). Furthermore, replacement of the C-3 acylamino substituent with reversed isosteres also provided highly potent analogs. Laurin, P. et al. *Biorgan. & Med. Chem. Lett.* 9: 2079 (1999). Recent studies also demonstrate a unique interaction of novobiocin with heat shock protein 90 (Hsp90), which shares homology with the a typical ATP-binding domaining of *E. coli* GyrB and stabilizes several oncogenic protein kinases. Marcu, M. G. *J. Nat. Cancer Inst.* 92: 242 (2000).

The gene cluster from *S. spheroides* which encodes for novobiocin biosynthesis and self resistance was recently cloned and a single glycosyltransferase gene (novM, accession AAF67506) was identified. Steffensky, M. et al. *Antimicrob. Agents Chemotherap.* 44: 1214 (2000). Given novobiocin contains a single saccharide, it is presumed novM encodes for the transfer of D-noviose from the activated dTDP-D-noviose to the aglycon novobiocic acid (FIG. 4, 20). The coumarins, while much more potent inhibitors of DNA gyrase in vitro than the clinically utilized quinolones, have failed clinically due to poor cell penetration, low solubility and toxicity in eukaryotes (perhaps due to this Hsp90 interaction). Thus, as an example of an area where engineering of secondary metabolites will be useful, glycosylated metabolites based on the coumarin aglycon but having altered carbohydrate moities may produce clinically useful compounds.

Both glycosyltransferases and nucleotidyltransferases play critical roles in the formation of glycosylated secondary metabolites. The first step in metabolite glycosylation is the reversible conversion of an α-D-hexose-1-phosphate to the corresponding nucleotide diphospho (NDP) hexose. Enzymes that catalyze this type of reaction (known as α-D-hexose-1-phosphate nucleotidyltransferases) are prevalent in nature and, regardless of their origins, are generally allosterically controlled with catalysis proceeding via an ordered bi-bi mechanism. Liu, H.-w. et al. "Pathways and Mechanisms in the Biogenesis of Novel Deoxysugars by Bacteria," *Annu. Rev. Microbiol.* 48: 223–256 (1994).

The culminating attachment of a carbohydrate to a secondary metabolite aglycon (or growing saccharide chain) is catalyzed by the family of enzymes known as glycosyltransferases. These enzymes transfer a sugar, from its activated form (a nucleotide diphospho-sugar or NDP-sugar), to an acceptor nucleophile to form a glycosidic bond and NDP. These enzymes can catalyze transfer with retention (with respect to the NDP-sugar) or inversion of anomeric stereochemistry. Drawing from the glycosidase analogy, the current belief is "retaining" glycosyltransferases proceed via a double displacement mechanism, which utilizes an enzyme-glycoside covalent intermediate, while the "inverting" transferases proceed via a single displacement mechanism. Sinnott, M. L. "Mechanisms of Glycosyl Hydrolysis and Transfer," *Chem. Rev.* 90: 1171–1202–1265 (1990). Based upon the known glycosylated metabolites, the majority of glycosyltransferases in secondary metabolism are "inverting" enzymes and the acceptor nucleophile is most often an aglycon or carbohydrate-derived heteroatom (O, N or S).

There are currently more than 70 putative secondary metabolite glycosyltransferase genes in the public database and these can be divided into three major families based upon sequence alignments. Thorson J. S. et al. (2001). Class I is the largest family and contains glycosyltransferases from both aromatic and macrolide metabolite pathways, Class II is predominately comprised of transferases associated with non-ribosomal peptides and glycolipids, while the majority of Class III enzymes are involved in metabolite inactivation. The number of known and putative secondary metabolite glycosyltransferase genes in the public database is growing rapidly, as this is an active area of research.

A number of genetic in vivo experiments have demonstrated that the glycosyltransferases of secondary metabolism (which include those for anthracyclines, angucyclines, nonribosomal peptides, macrolides and enediynes) are promiscuous with respect to the NDP-sugar donor. Thorson J. S. et al. (2001); Hutchinson, C. R. "Combinatorial Biosynthesis for New Drug Discovery," *Curr. Opin. Microbiol.* 1: 319–329 (1998). While these in vivo experiments have provided novel metabolites, the newly formed metabolites, in most cases, were inactivated via host-catalyzed modification to prevent killing the host producing organism. Thus, in biosynthetically altering glycosylation, an in vitro scheme is desirable to eliminate this interference by host inactivation mechanisms.

The glycosyltransferases of secondary metabolism rely almost exclusively upon pyrimidine (uridine or thymidine) diphosphosugars, yet, in vitro studies in this area are severely lacking due to the inability to access the appropriate NDP-sugar substrates. Easy access to UDP- or dTDP-sugars would revolutionize the biochemical characterization and exploitation of these critical glycosyltransferases.

Surprisingly, a three dimensional structure for any enzyme from this important class of enzymes is lacking and of the many nucleotidyltransferases studied, the dTDP-α-D-glucose forming thymidylyltransferases have received the least attention. The best characterized thymidylyltransferase (rmlA-encoded $E_p$) is from *Salmonella*, which catalyzes the reaction shown in FIG. 2*a*. Lindquist, L. et al. "Purification, Characterization and HPLC Assay of Salmonella Glucose-1-phosphate Thymidylyltransferase from the Cloned rfbA Gene," *Eur. J. Biochem.* 211: 763–770 (1993). Preliminary $E_p$ substrate specificity studies, limited to only a few commercially available hexopyranosyl phosphates and NTPs, revealed $E_p$ could utilize both dTTP and UTP as well as α-D-glucosamine-1-phosphate as a substitute for natural substrate (α-D-glucose-1-phosphate). Kinetic analysis revealed a ping-pong mechanism with $K_m$ values for the forward direction for dTTP and α-D-glucose-1-phosphate of 0.02 mM and 0.11 mM, respectively. In the reverse reaction the $K_m$ values for dTDP-α-D-glucose and diphosphate were 0.083 mM and 0.15 mM, respectively. Lindquist, L. et al. (1993).

The above examples illustrate that carbohydrate ligands often define the biological activity of a particular secondary metabolite and suggest alteration of saccharide ligands should lead to new compounds which may display novel biological activity. However, the complex structure of most glycosylated natural products preclude the ability to synthetically exchange their sugar ligands.

Further, while in vivo experiments have provided novel metabolites, the newly formed metabolites, in most cases, were inactivated via host-catalyzed modification to prevent killing the host producing organism. As the organisms producing the novel metabolites are killed, it is not feasible to produce sufficient amounts of novel metabolites for analysis or therapeutic use in in vivo systems. Additionally, producing novel metabolites in vivo requires the use of recombinant DNA technology to alter gene expression. Such methods are too time consuming for rapid production of numerous novel metabolites for testing as drug candidates. Further still, the production of these new agents was also severely limited by the host's biosynthetic machinery so that the number and diversity of compounds that may be produced by such methods is likewise severely limited.

Thus, for biosynthetically altering glycosylation, an in vitro scheme is needed to eliminate the problems associated with in vivo manipulation. Further, a scheme that allows such manipulation despite the complexities of biologically active secondary metabolites is needed.

SUMMARY OF THE INVENTION

The present invention provides combinatorial methods for rapidly generating a diverse library of glycorandomized structures, comprising incubating one or more aglycons and a pool of NDP-sugars in the presence of a glycosyltransferase. The glycosyltransferase may be one that is associated with or involved in production of natural secondary metabolites, or one which is putatively associated with or involved in production of natural secondary metabolites. The glycosyltransferase may show significant flexibility with respect to its NDP-sugar donors and/or its aglycons. NDP-sugar donors may be commercially available, or may be produced by utilizing mutant or wild type nucleotidyl-transferases significant flexibility with respect to their substrates.

The present invention provides a novel method of chemo-enzymatic synthesis of glycosylated entities. The present invention provides a simple and efficient method to bypass the severe barriers to synthesis posed by both the complexities of biologically active secondary metabolites and the difficulties and limitations of in vivo manipulation, for the first time providing the ability to construct large libraries of diverse macrolides with varied carbohydrate attachments as therapeutic candidates and for use in, e.g., biomedical processes, production of downstream compounds, and biomedical and chemical research.

The present invention enables the rapid synthesis of compounds (typically based upon natural products) too complex for chemical synthesis but not accessible by biosynthesis.

The present invention enables the rapid generation of libraries of novel chemical entities not available through synthesis or biosynthesis. Since these compounds are generally based on biologically active natural products and the carbohydrate ligands being randomized are generally critical to this activity, the potential for compounds with novel activities is great.

The present invention provides methods of glycorandomization and methods for producing novel compounds through the use of glycorandomization.

The present invention provides methods for producing novel glycosylated entities. The present invention provides chemo-enzymatic methods for altering any given glycosylated entity or entity capable of being glycosylated to produce novel entities. In a preferred embodiment of the present invention, novel entities with enhanced or unique biological activities are produced. Entities which may be altered include, but are not limited to, natural and synthetic aglycons, natural product metabolites, enediynes, anthracyclines, angucyclines, aureolic acids, orthosomycins, macrolides, aminoglycosides, non-ribosomal peptides, polyenes, steroids, lipids, indolocarbazoles, bleomycins, amicetins, benzoisochromanequinones coumarins, polyketides, pluramycins, aminoglycosides, oligosaccharides, peptides, proteins, numerous other classes of bioactive compounds, and hybrids consisting of one or more these components.

In one embodiment, a method of the present invention comprises incubating a pool of entities capable of being glycosylated with a glycosyltransferase (which may also be referred to herein as glycosyltransferases) and a pool of nucleotidyl sugars to produce a glycosylated entity.

In certain embodiments, the pool of sugars consists of a single sugar. In other embodiments, the pool of sugars comprises different sugars. In one such embodiment, the pool of sugars comprises a population of sugars that is highly diverse. In certain embodiments, the pool of sugars comprises known nucleotidyl sugars and/or novel nucleotidyl sugars.

In certain embodiments, the pool of NDP-sugar donors comprises naturally occurring sugars. In certain embodiments, the pool of NDP-sugar donors comprises novel or "unnatural" sugars. In certain embodiments the pool of NDP-sugar donors comprises or is selected from a library or libraries of NDP-sugars catalyzed by utilizing the promiscuity of wild type and/or engineered *Salmonella enterica* LT2 α-D-glucopyranosyl phosphate thymidylyltransferase (Ep).

In certain embodiments, at least one of the at least one nucleotide sugar is selected from the group consisting of Uridine 5'-(α-D-allopyranosyl diphosphate); Uridine 5'-(α-D-altropyranosyl diphosphate); Thymidine 5'-(α-D-gulopyranosyl diphosphate); Uridine 5'-(α-D-gulopyranosyl diphosphate); Thymidine 5'-(α-D-idopyranosyl diphosphate); Uridine 5'-(α-D-idopyranosyl diphosphate); Thymidine 5'-(α-D-talopyranosyl diphosphate); Uridine 5'-(α-D-talopyranosyl diphosphate); Thymidine 5'-(6-amino-6-deoxy-α-D-glucopyranosyl diphosphate); Uridine 5'-(6-amino-6-deoxy-α-D-glucopyranosyl diphosphate); Thymidine 5'-(4-amino-4-deoxy-α-D-glucopyranosyl diphosphate); Uridine 5'-(4-amino-4-deoxy-α-D-glucopyranosyl diphosphate); Thymidine 5'-(3-amino-3-deoxy-α-D-glucopyranosyl diphosphate); Uridine 5'-(3-amino-3-deoxy-α-D-glucopyranosyl diphosphate); Thymidine 5'-(2-amino-2-deoxy-α-D-glucopyranosyl diphosphate); Uridine 5'-(2-amino-2-deoxy-α-D-glucopyranosyl diphosphate); Thymidine 5'-(6-acetamido-6-deoxy-α-D-glucopyranosyl diphosphate); Uridine 5'-(6-acetamido-6-deoxy-α-D-glucopyranosyl diphosphate); Thymidine 5'-(4-acetamido-4-deoxy-α-D-glucopyranosyl diphosphate); Uridine 5'-(4-acetamido-4-deoxy-α-D-glucopyranosyl diphosphate); Thymidine 5'-(3-acetamido-3-deoxy-α-D-glucopyranosyl diphosphate); Uridine 5'-(3-acetamido-3-deoxy-α-D-glucopyranosyl diphosphate); Thymidine 5'-(2-acetamido-2-deoxy-α-D-glucopyranosyl diphosphate); Uridine 5'-(2-acetamido-2-deoxy-α-D-glucopyranosyl diphosphate); Thymidine 5'-(4-amino-4,6- dideoxy-α-D-glucopyranosyl diphosphate); Uridine 5'-(4-amino-4,6-dideoxy-α-D-glucopyranosyl diphosphate); Thymidine 5'-(α-D-glucopyran-6-uronic acid diphosphate); Uridine 5'-(α-D-glucopyran-6-uronic acid diphosphate); Thymidine 5'-(α-D-arabinopyranosyl diphosphate); Uridine 5'-(α-D-arabinopyranosyl diphosphate); and

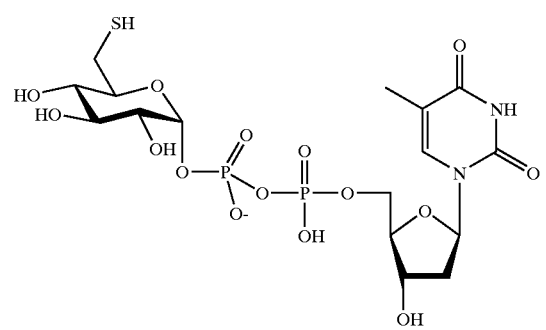

$C_{16}H_{25}N_2O_{15}P_2S^-$
Exact Mass: 579.05
Determined: 579.06

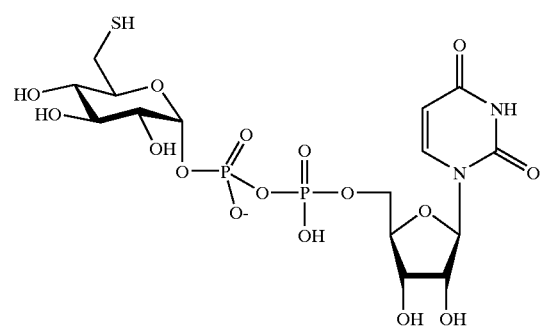

$C_{15}H_{23}N_2O_{16}P_2S^-$
Exact Mass: 581.02
Determined: 581.02

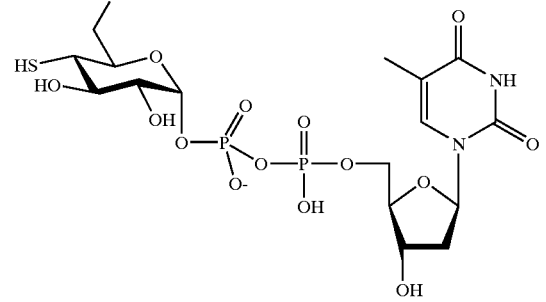

$C_{16}H_{25}N_2O_{15}P_2S^-$
Exact Mass: 579.05
Determined: 579.08

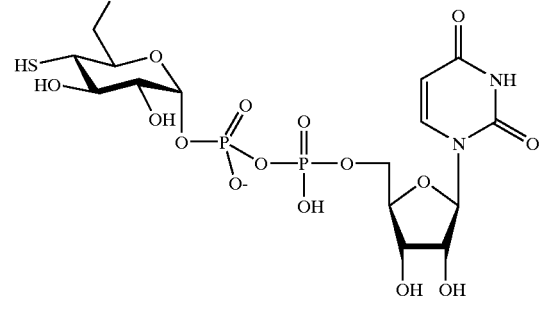

$C_{15}H_{23}N_2O_{16}P_2S^-$
Exact Mass: 581.02
Determined: 581.01

-continued

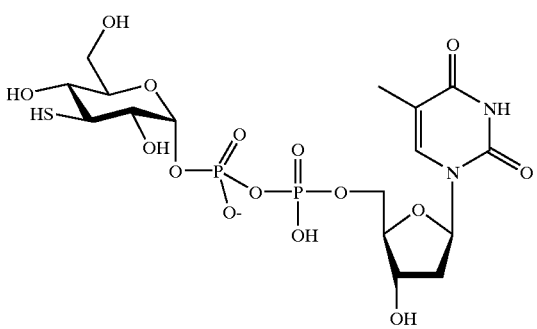

$C_{16}H_{25}N_2O_{15}P_2S^-$
Exact Mass: 579.05
Determined: 579.02

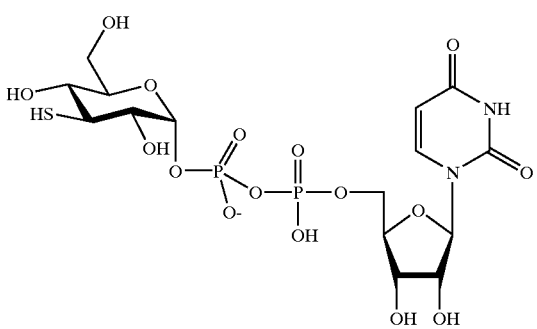

$C_{15}H_{23}N_2O_{16}P_2S^-$
Exact Mass: 581.02
Determined: 581.05

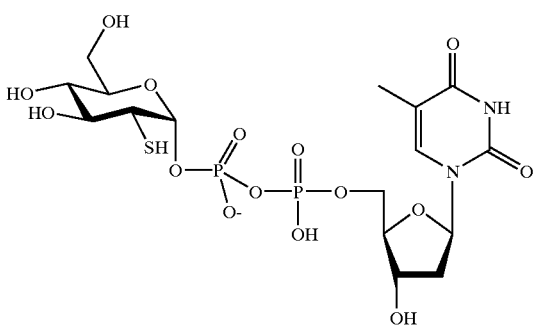

$C_{16}H_{25}N_2O_{15}P_2S^-$
Exact Mass: 579.05
Determined: 579.10

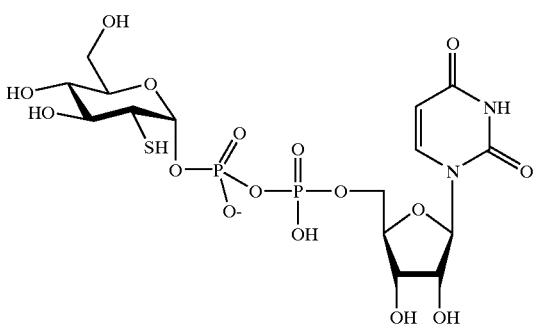

$C_{15}H_{23}N_2O_{16}P_2S^-$
Exact Mass: 581.02
Determined: 581.08

11
-continued
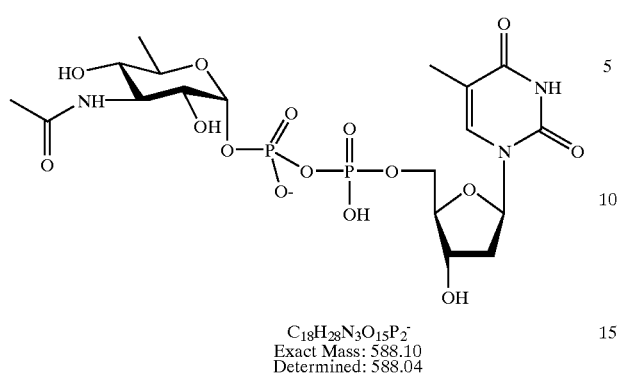
C₁₈H₂₈N₃O₁₅P₂⁻
Exact Mass: 588.10
Determined: 588.04
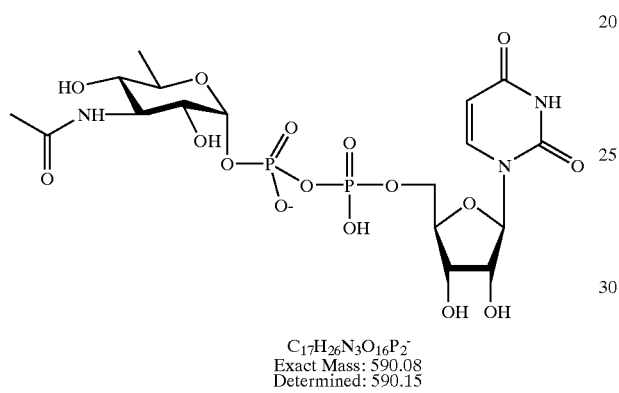
C₁₇H₂₆N₃O₁₆P₂⁻
Exact Mass: 590.08
Determined: 590.15
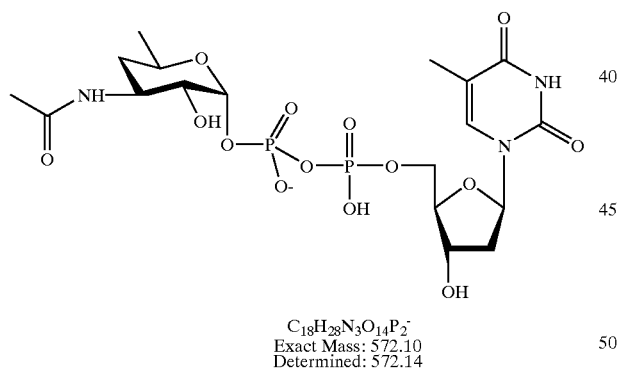
C₁₈H₂₈N₃O₁₄P₂⁻
Exact Mass: 572.10
Determined: 572.14
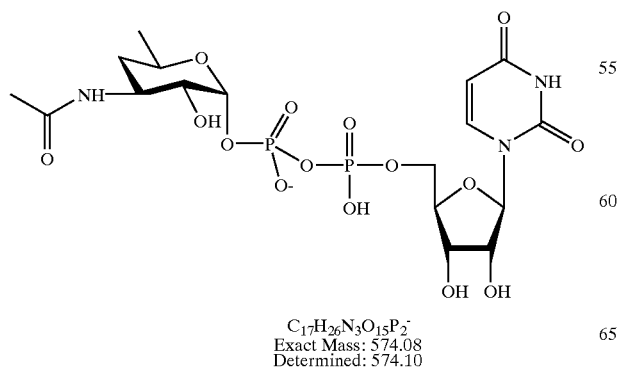
C₁₇H₂₆N₃O₁₅P₂⁻
Exact Mass: 574.08
Determined: 574.10
12
-continued
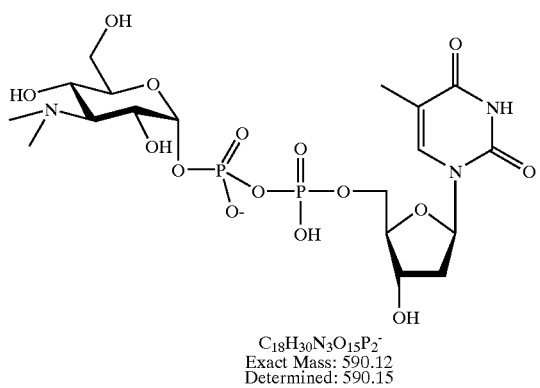
C₁₈H₃₀N₃O₁₅P₂⁻
Exact Mass: 590.12
Determined: 590.15
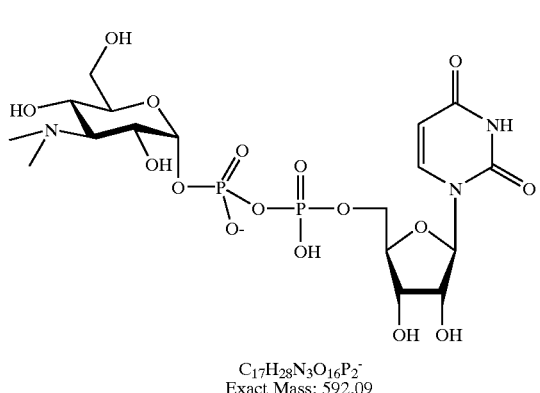
C₁₇H₂₈N₃O₁₆P₂⁻
Exact Mass: 592.09
Determined: 592.09
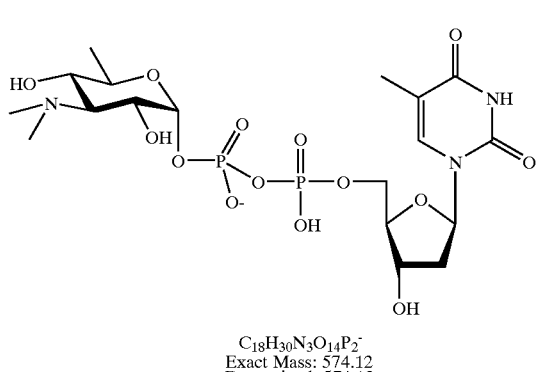
C₁₈H₃₀N₃O₁₄P₂⁻
Exact Mass: 574.12
Determined: 574.12
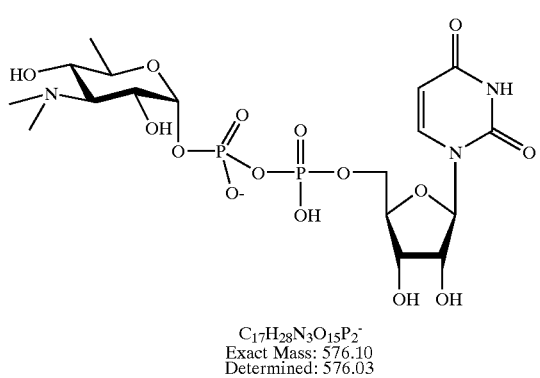
C₁₇H₂₈N₃O₁₅P₂⁻
Exact Mass: 576.10
Determined: 576.03

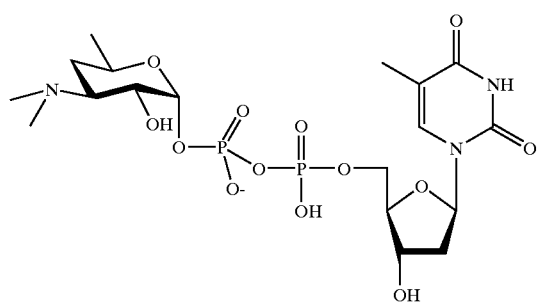
C₁₈H₃₀N₃O₁₃P₂⁻
Exact Mass: 558.13
Determined: 558.17
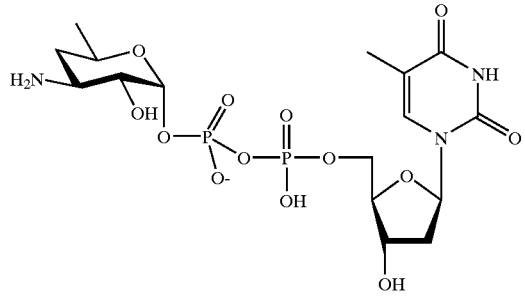
C₁₆H₂₆N₃O₁₃P₂⁻
Exact Mass: 530.09
Determined: 530.04
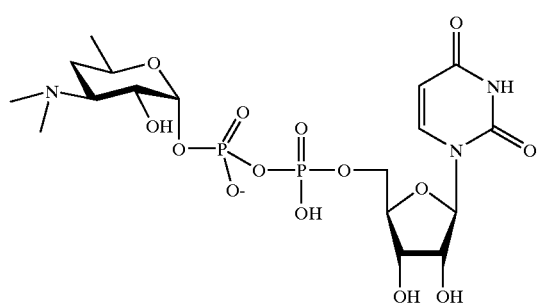
C₁₇H₂₈N₃O₁₄P₂⁻
Exact Mass: 560.10
Determined: 560.15
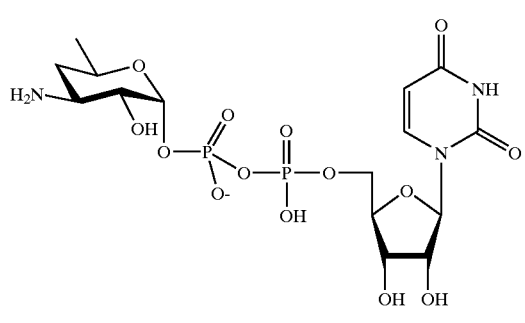
C₁₅H₂₄N₃O₁₄P₂⁻
Exact Mass: 532.07
Determined: 532.10
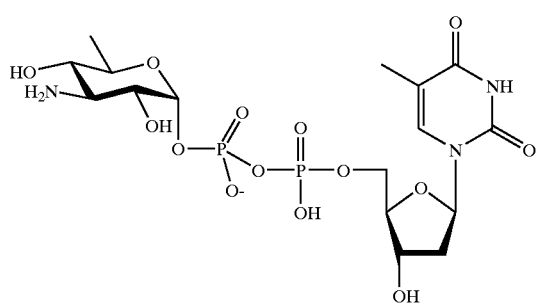
C₁₆H₂₆N₃O₁₄P₂⁻
Exact Mass: 546.09
Determined: 546.05
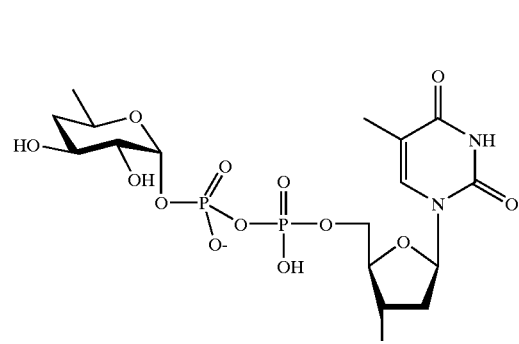
C₁₆H₂₅N₂O₁₄P₂⁻
Exact Mass: 531.08
Determined: 531.07
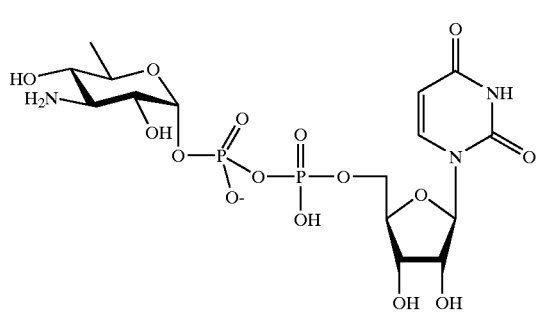
C₁₅H₂₄N₃O₁₅P₂⁻
Exact Mass: 548.07
Determined: 548.13
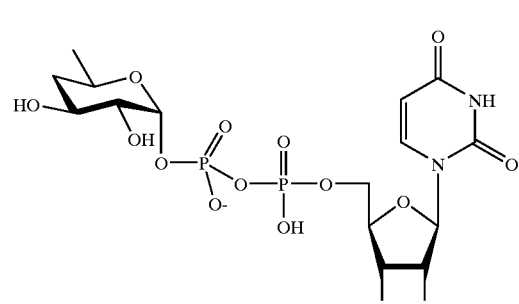
C₁₅H₂₃N₂O₁₅P₂⁻
Exact Mass: 533.06
Determined: 533.09

In certain other embodiments, at least one of the at least one nucleotide sugar is selected from the group consisting of Thymidine 5'-(α-D-glucopyranosyl diphosphate); Uridine 5'-(α-D-glucopyranosyl diphosphate); Thymidine 5'-(2-deoxy-α-D-glucopyranosyl diphosphate); Uridine 5'-(2-deoxy-α-D-glucopyranosyl diphosphate); Thymidine 5'-(3-deoxy-α-D-glucopyranosyl diphosphate); Uridine 5'-(3-deoxy-α-D-glucopyranosyl diphosphate); Thymidine 5'-(4-deoxy-α-D-glucopyranosyl diphosphate); Uridine 5'-(4-deoxy-α-D-glucopyranosyl diphosphate); Thymidine 5'-(6-deoxy-α-D-glucopyranosyl diphosphate); Uridine 5'-(6-deoxy-α-D-glucopyranosyl diphosphate); Thymidine 5'-(α-D-mannopyranosyl diphosphate); Uridine 5'-(α-D-mannopyranosyl diphosphate); Thymidine 5'-(α-D-galactopyranosyl diphosphate); Uridine 5'-(α-D-galactopyranosyl diphosphate); Thymidine 5'-(α-D-allopyranosyl diphosphate); and Thymidine 5'-(α-D-altropyranosyl diphosphate).

The present invention provides a method for producing novel glycosylated compounds comprising: combining at least one moiety capable of being glycosylated and at least one first nucleotide sugar in the presence of at least one first glycosyltransferase, wherein the method is carried out in vitro and at least one novel glycosylated compound is produced.

The present invention provides a method comprising combining (a) at least one moiety capable of being glycosylated and (b) at least one first nucleotide sugar produced by combining nucleotide triphosphate (NTP) and at least one sugar phosphate in the presence of at least one mutated nucleotidyltransferase; in the presence of at least one first glycosyltransferase, wherein at least one glycosylated compound is produced.

In certain embodiments, at least one of the at least one mutated nucleotidyltransferase is $E_p$ mutated at one or more amino acids selected from the group consisting of V173, G147, W224, N112, G175, D111, E162, T201, I200, E199, R195, L89, L89T, L109, Y146 and Y177. In certain embodiments, at least one of the at least one mutated nucleotidyltransferase is $E_p$ mutated at one or more amino acids in its active site, its divalent cation binding site, and/or its auxiliary site.

Methods according to the present invention are preferably carried out in vitro.

In certain preferred embodiments, at least on of the at least one novel glycosylated compounds produced has enhanced and/or unique biological activity as compared to at least one of the at least one moieties capable of being glycosylated. In certain other preferred embodiments, more than one type of glycosylated compound is produced in a single reaction vessel and at least one of the at least one glycosylated compounds produced is a novel glycosylated compound.

In certain other preferred embodiments, highly diverse population of glycosylated compounds is produced and at least one of the at least one glycosylated compounds produced is a novel glycosylated compound.

In certain embodiments, at least one of the at least one moiety capable of being glycosylated is selected from the group consisting of natural and synthetic metabolites, pyran rings, furan rings, enediynes, anthracyclines, angucyclines, aureolic acids, orthosomycins, macrolides, aminoglycosides, non-ribosomal peptides, polyenes, steroids, lipids, indolocarbazoles, bleomycins, amicetins, benzoisochromanequinones coumarins, polyketides, pluramycins, aminoglycosides, oligosaccharides, peptides, proteins, and hybrids thereof.

In certain other embodiments, at least one of the at least one moiety capable of being glycosylated is selected from the group consisting of aglycons of bioactive anthracyclines, angucyclines, nonribosomal peptides, macrolides, enediynes, indolocarbazoles, pluramycins, aurelolic acids, orthosomycins, aminoglycosides, coumarins, bleomycins, amicetins, polyenes, benzoisochromanequinones, angucyclines, and hybrids thereof.

In certain other embodiments, at least one of the at least one moiety capable of being glycosylated is selected from the group consisting of enediynes, anthracyclines, angucyclines, aureolic acids, orthosomycins, macrolides, aminoglycosides, non-ribosomal peptides, polyenes, steroids, lipids, indolocarbazoles, bleomycins, amicetins, benzoisochromanequinones coumarins, polyketides, pluramycins, aminoglycosides, oligosaccharides, peptides, proteins, and hybrids consisting of one or more these components.

In certain embodiments, at least one of the at least one first glycosyltransferase is selected from the group consisting of CalB, CalE, CalN, CalU, Gra orfl4, Gra orf5, LanGT1, LanGT2, LanGT3, LanGT4, MtmGI, MtmGII, MtmGIII, MtmGTIV, NovM, RhlB, Rif orf7, SnogD, SnogE, SnogZ, UrdGT1a, UrdGT1b, UrdGT1c, UrdGT2, AknK, AknS, DesVII, DnrS, OleG1, OleG2, TylCV, TylMII, TylN, DauH, DnrH, EryBV, EryCIII, Ngt, BgtA, BgtB, BgtC, GftA, GftB, GftC, GftD, GftE, Gp1-1, Gp1-2, RtfA, AveBI, BlmE, BlmF, MgtA, NysD1, OleD, OleI, SpcF, SpcG, StrH, Ugt51B1, Ugt51C1, UGT52, UgtA, UgtB, UgtC, UgtD and homologs thereof; is selected from the group consisting of those glycosyltransferases known to be involved in the synthesis of bioactive metabolites; or is is produced by expressing the product of a putative glycosyltransferase gene.

In certain embodiments, more than one moiety capable of being glycosylated is incubated with the at least one novel nucleotide sugar in the presence at least one type of glycosyltransferase.

In certain embodiments, at least one moiety capable of being glycosylated is incubated with more than one novel nucleotide sugar in the presence more than one type of glycosyltransferase.

In certain embodiments, at least one moiety capable of being glycosylated is incubated with the at least one novel nucleotide sugar in the presence more than one type of glycosyltransferase.

The present invention also provides a method comprising incubating at least one glycosylated compound produced by the method of claim C that is capable of being glycosylated with and at least one second nucleotide sugar in the presence of at least one second glycosyltransferase to produce at least one twice-glycosylated compound having at least a first and a second glycosyl attachment, wherein the first and second may be of the same type or of different types and the second glycosyl attachment may be attached to the original moiety capable of being glycosylated or to the first glycosyl attachment.

The present invention provides a method comprising subjecting at least one glycosylated compound produced according to the methods of the present invention to repeated cycles of incubation with at least one nucleotide sugar in the presence of at least one glycosyltransferase until a population multiply-glycosylated compounds of the desired type and size is achieved.

The present invention also provides novel compounds produced by the methods of the present invention. Nonlimiting examples of the such novel compounds that are provided by the present invention include two novel novobiocin (designated Nov-1 and Nov-2) derivatives and six novel erythromycin (designated Ery-1-Ery-6) analogs.

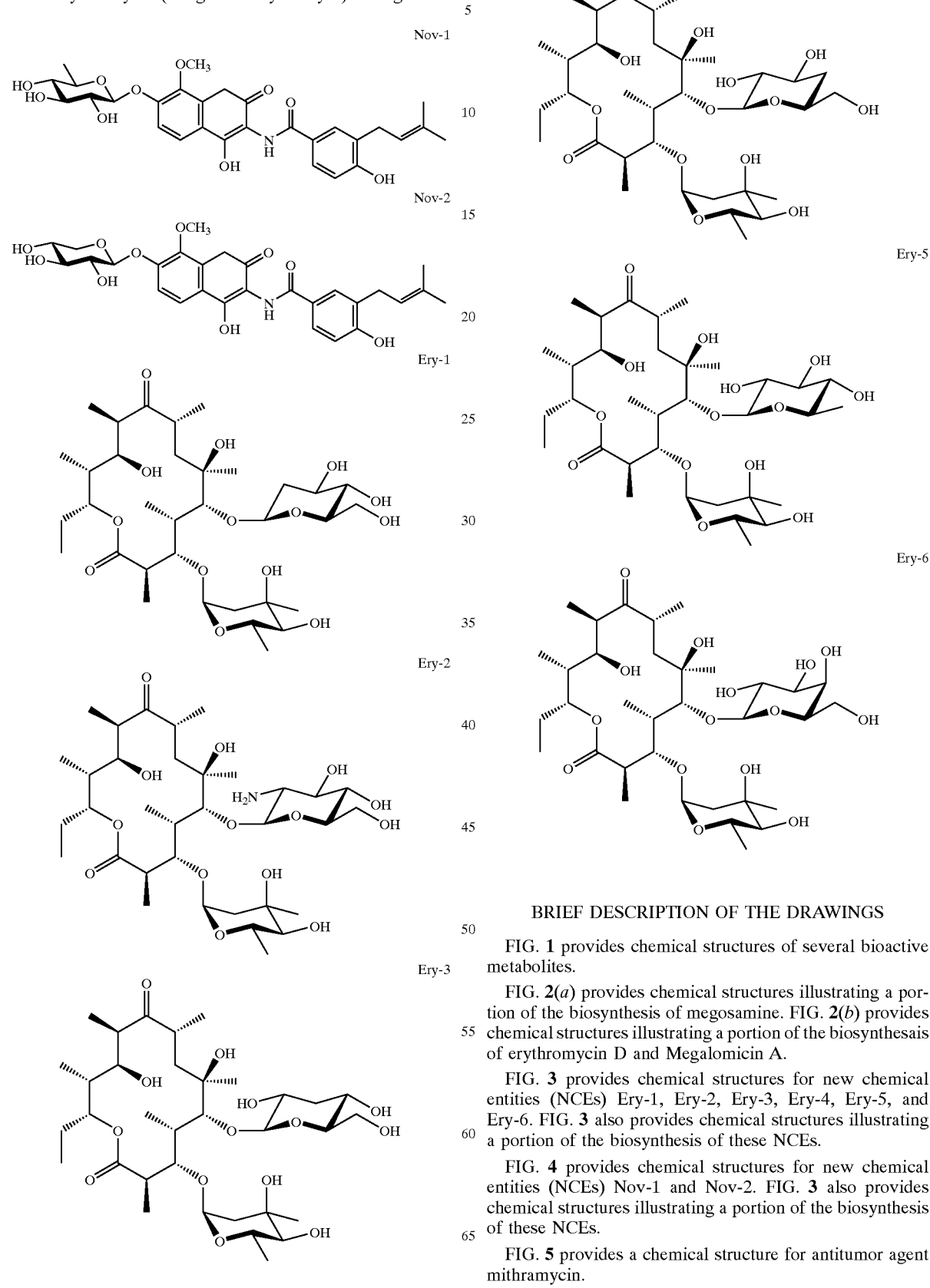

BRIEF DESCRIPTION OF THE DRAWINGS

FIG. 2(*b*) provides chemical structures illustrating a portion of the biosynthesais of erythromycin D and Megalomicin A.

FIG. 3 also provides chemical structures illustrating a portion of the biosynthesis of these NCEs.

FIG. 3 also provides chemical structures illustrating a portion of the biosynthesis of these NCEs.

DETAILED DESCRIPTION OF THE INVENTION

The present invention provides a simple and efficient method to bypass the severe barriers to synthesis posed by both the complexities of biologically active secondary metabolites and the difficulties and limitations of in vivo manipulation, for the first time providing the ability to construct large and diverse libraries macrolides with varied carbohydrate attachments.

The present invention utilizes the promiscuity of nucleotidyltransferases and glycosyltransferases for their respective substrates and donor molecules to provide a method for producing libraries of glycosylated entities, which then may be screened by methods known in the art for compounds useful in, e.g., clinical therapy, biomedical research, and chemical synthesis of downstream products.

A number of genetic in vivo experiments have demonstrated that the glycosyltransferases of secondary metabolism (which include those for anthracyclines, angucyclines, nonribosomal peptides, macrolides and enediynes) are promiscuous with respect to the NDP-sugar donor.

However, prior in vitro studies in this area were severely limited due to the inability to access the appropriate NDP-sugar substrates.

Figure 1:
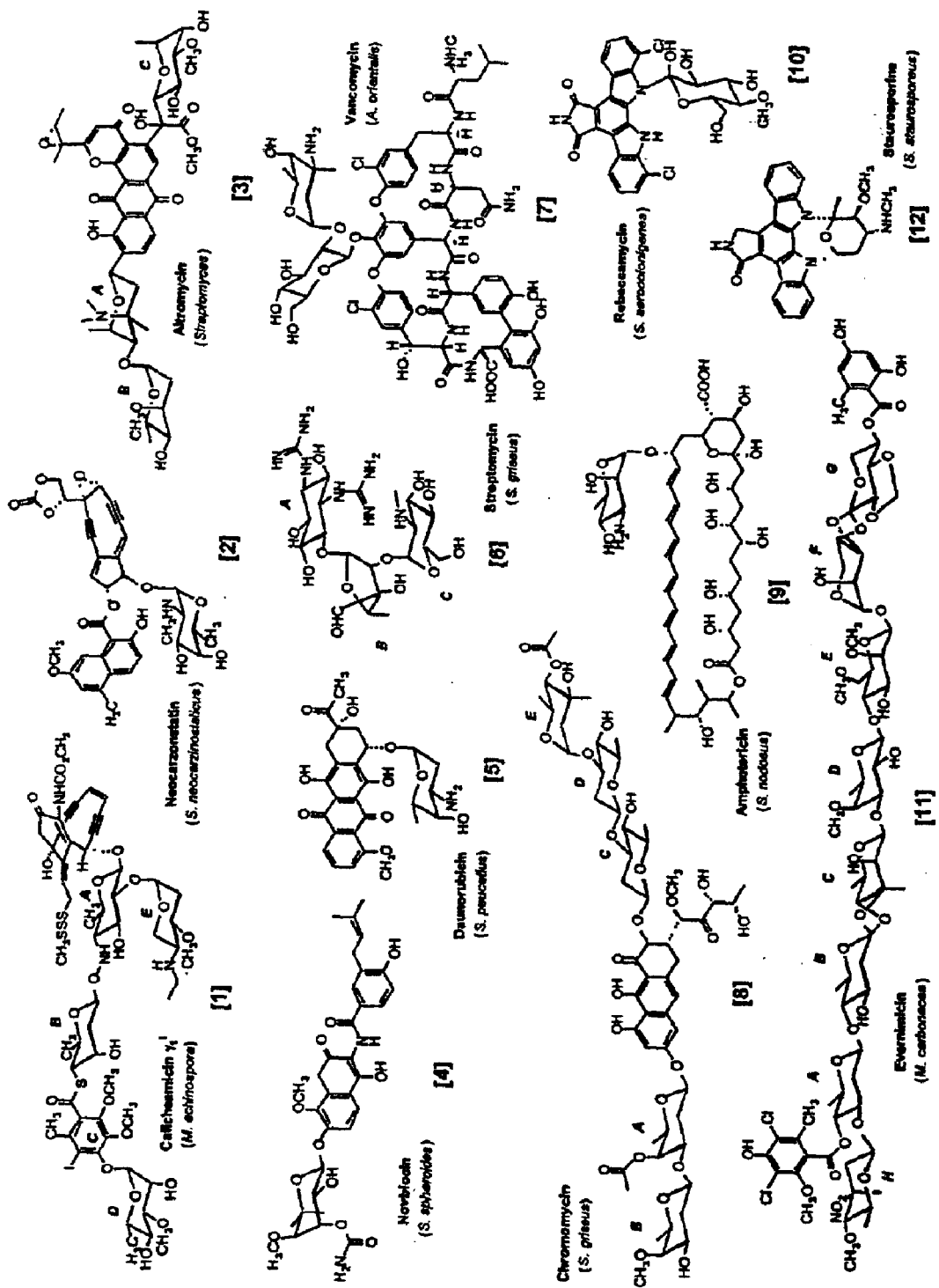
FIG. 1 provides chemical structures of several bioactive metabolites.
Figure 2:
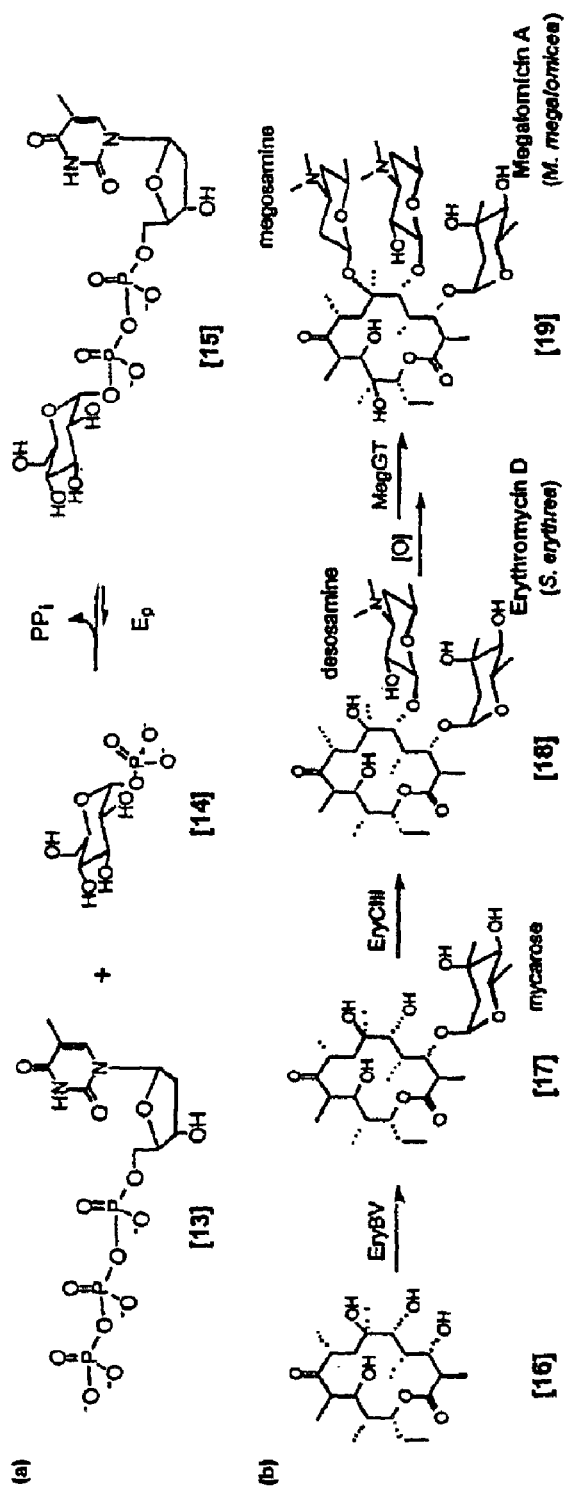
FIG. 2(*a*) provides chemical structures illustrating a portion of the biosynthesis of megosamine.

The present inventors recently vastly increased the pool of UDP- and dTDP-sugar substrates available by systematically re-examining the substrate specificity of purified $E_p$, which revealed this enzyme can accommodate a wide array of hexopyranosyl phosphates as a replacement for FIG. 2, 14 in this reaction. See, e.g., Jiang J, et al., "Expanding the Pyrimidine Diphosphosugar Repertoire: The Chemoenzymatic Synthesis of Amino- and Acetamidoglucopyranosyl Derivatives" *Angew Chem Int Ed Engl* 40(8): 1502–1505 (2001); Jiang J, et al., "A General Enzymatic Method for the Synthesis of Natural and 'Unnatural' UDP- and TDP-Nucleotide Sugars," *Journal of the American Chemical Society* 122(28): 6803–6804 (2000).

In comparison to the tedious chemical synthesis of nucleotide sugars, this one-step $E_p$-catalyzed enzymatic conversion is a rapid and effective method to construct libraries of both the desired UDP- and dTDP-nucleotide diphosphosugars for in vitro glycorandomization. As a result, an enormous number of UDP- and dTDP-sugar substrates can be produced, including sugars that were difficult or impossible to produce in vitro prior to the teachings of the present inventors and sugars that have never been produced before. Such nucleotide sugars can be used in the methods of the present invention to produce an enormous number of glycosylated compounds, including glycosylated compounds that were difficult or impossible to produce in vitro prior to the teachings of the present inventors and glycosylated compounds that have never been produced before.

"Novel" nucleotide sugars, as used herein, refer to nucleotide sugars which have not been made in vitro prior to the teachings of the present inventors in the references cited herein, or to nucleotide sugars which have never been produced synthetically prior to the teachings of the present inventors in the references cited herein, or to nucleotide sugars that are completely novel and have never been produced via natural or chemical synthesis. Likewise, "novel" glycosylated compounds, as used herein, refer to glycosylated compounds which have not been made in vitro prior to the teachings of the present inventors in the references cited herein, or to glycosylated compounds which have never been produced synthetically prior to the teachings of the present inventors in the references cited herein, or to glycosylated compounds that are completely novel and have never been produced via natural or chemical synthesis.

Exemplary nucleotide sugars which may be used in methods according to the present invention include, but are not limited to: Thymidine 5'-(α-D-glucopyranosyl diphosphate); Uridine 5'-(α-D-glucopyranosyl diphosphate); Thymidine 5'-(2-deoxy-α-D-glucopyranosyl diphosphate); Uridine 5'-(2-deoxy-α-D-glucopyranosyl diphosphate); Thymidine 5'-(3-deoxy-α-D-glucopyranosyl diphosphate); Uridine 5'-(3-deoxy-α-D-glucopyranosyl diphosphate); Thymidine 5'-(4-deoxy-α-D-glucopyranosyl diphosphate); Uridine 5'-(4-deoxy-α-D-glucopyranosyl diphosphate); Thymidine 5'-(6-deoxy-α-D-glucopyranosyl diphosphate); Uridine 5'-(6-deoxy-α-D-glucopyranosyl diphosphate); Thymidine 5'-(α-D-mannopyranosyl diphosphate); Uridine 5'-(α-D-mannopyranosyl diphosphate); Thymidine 5'-(α-D-galactopyranosyl diphosphate); Uridine 5'-(α-D-galactopyranosyl diphosphate); Thymidine 5'-(α-D-allopyranosyl diphosphate); Thymidine 5'-(α-D-altropyranosyl diphosphate); Uridine 5'-(α-D-allopyranosyl diphosphate); Uridine 5'-(α-D-altropyranosyl diphosphate); Thymidine 5'-(α-D-gulopyranosyl diphosphate); Uridine 5'-(α-D-gulopyranosyl diphosphate); Thymidine 5'-(α-D-idopyranosyl diphosphate); Uridine 5'-(α-D-idopyranosyl diphosphate); Thymidine 5'-(α-D-talopyranosyl diphosphate); Uridine 5'-(α-D-talopyranosyl diphosphate); Thymidine 5'-(6-amino-6-deoxy-α-D-glucopyranosyl diphosphate); Uridine 5'-(6-amino-6-deoxy-α-D-glucopyranosyl diphosphate); Thymidine 5'-(4-amino-4-deoxy-α-D-glucopyranosyl diphosphate); Uridine 5'-(4-amino-4-deoxy-α-D-glucopyranosyl diphosphate); Thymidine 5'-(3-amino-3-deoxy-α-D-glucopyranosyl diphosphate); Uridine 5'-(3-amino-3-deoxy-α-D-glucopyranosyl diphosphate); Thymidine 5'-(2-amino-2-deoxy-α-D-glucopyranosyl diphosphate); Uridine 5'-(2-amino-2-deoxy-α-D-glucopyranosyl diphosphate); Thymidine 5'-(6-acetamido-6-deoxy-α-D-glucopyranosyl diphosphate); Uridine 5'-(6-acetamido-6-deoxy-α-D-glucopyranosyl diphosphate); Thymidine 5'-(4-acetamido-4-deoxy-α-D-glucopyranosyl diphosphate); Uridine 5'-(4-acetamido-4-deoxy-α-D-glucopyranosyl diphosphate); Thymidine 5'-(3-acetamido-3-deoxy-α-D-glucopyranosyl diphosphate); Uridine 5'-(3-acetamido-3-deoxy-α-D-glucopyranosyl diphosphate); Thymidine 5'-(2acetamido-2-deoxy-α-D-glucopyranosyl diphosphate); Uridine 5'-(2-acetamido-2-deoxy-α-D-glucopyranosyl diphosphate); Thymidine 5'-(4-amino-4,6-dideoxy-α-D-glucopyranosyl diphosphate); Uridine 5'-(4-amino-4,6-dideoxy-α-D-glucopyranosyl diphosphate); and

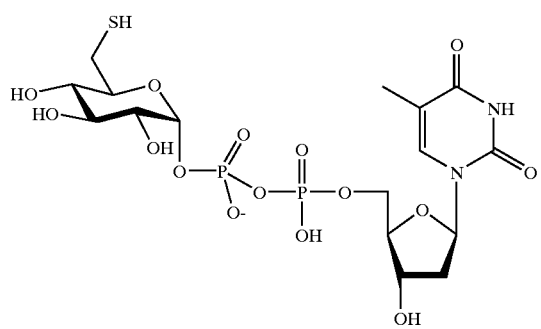

$C_{16}H_{25}N_2O_{15}P_2S^-$
Exact Mass: 579.05
Determined: 579.06

-continued
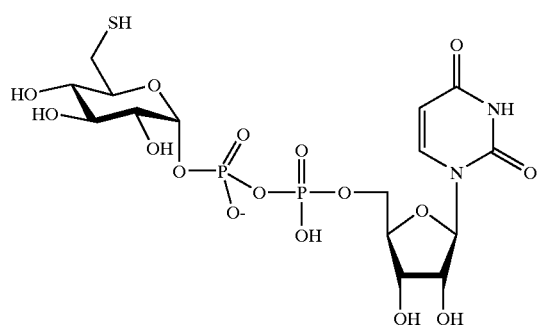
C₁₅H₂₃N₂O₁₆P₂S⁻
Exact Mass: 581.02
Determined: 581.02
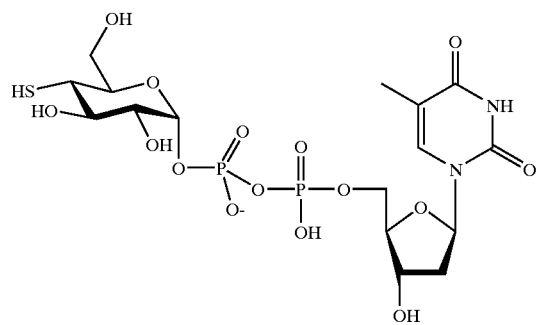
C₁₆H₂₅N₂O₁₅P₂S⁻
Exact Mass: 579.05
Determined: 579.08
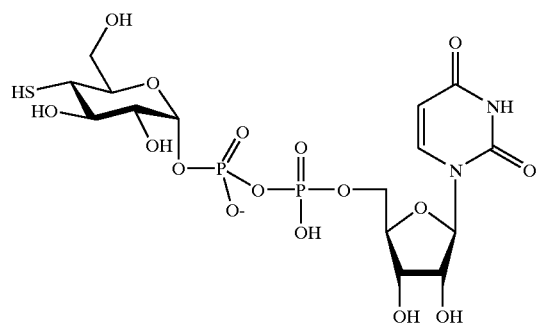
C₁₅H₂₃N₂O₁₆P₂S⁻
Exact Mass: 581.02
Determined: 581.01
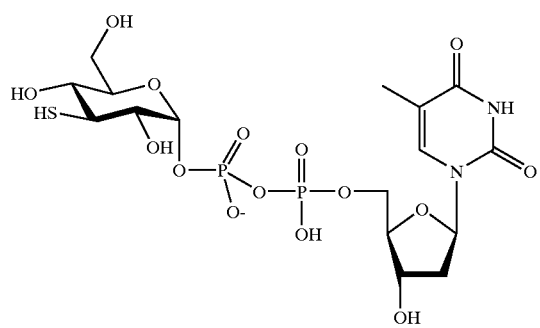
C₁₆H₂₅N₂O₁₅P₂S⁻
Exact Mass: 579.05
Determined: 579.02
-continued
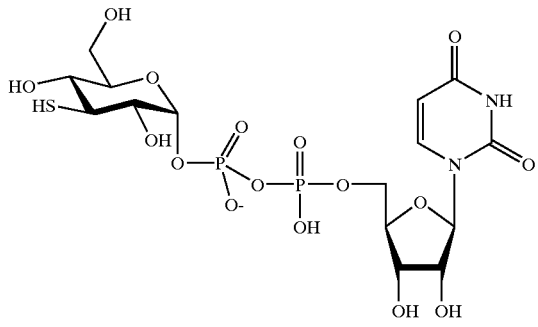
C₁₅H₂₃N₂O₁₆P₂S⁻
Exact Mass: 581.02
Determined: 581.05
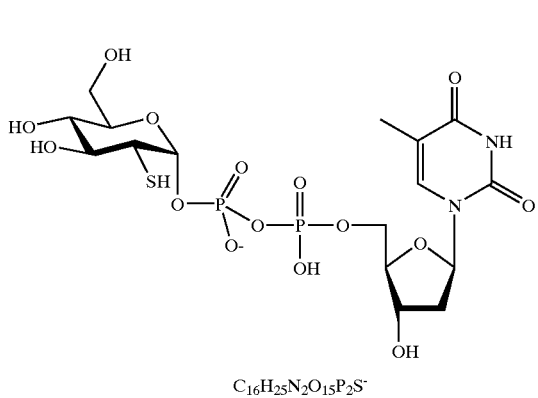
C₁₆H₂₅N₂O₁₅P₂S⁻
Exact Mass: 579.05
Determined: 579.10
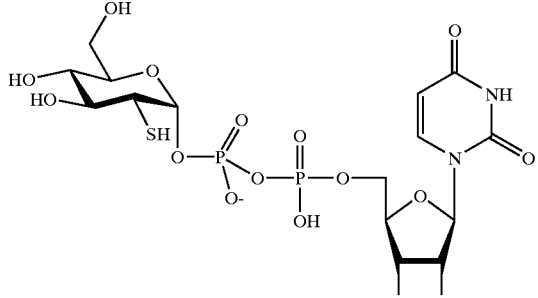
C₁₅H₂₃N₂O₁₆P₂S⁻
Exact Mass: 581.02
Determined: 581.08
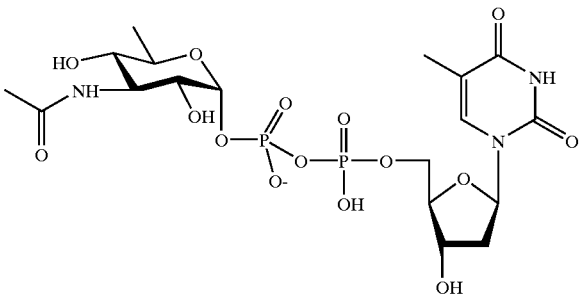
C₁₈H₂₈N₃O₁₅P₂⁻
Exact Mass: 588.10
Determined: 588.04

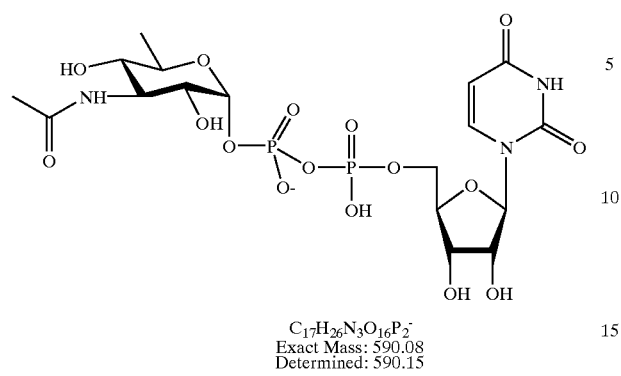
C₁₇H₂₆N₃O₁₆P₂⁻
Exact Mass: 590.08
Determined: 590.15
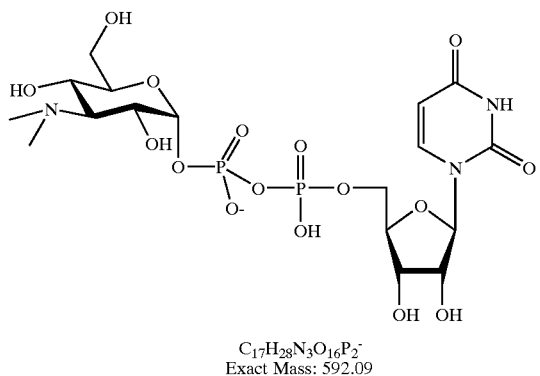
C₁₇H₂₈N₃O₁₆P₂⁻
Exact Mass: 592.09
Determined: 592.09
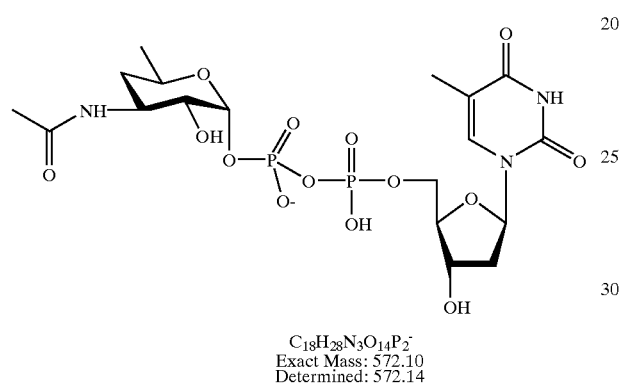
C₁₈H₂₈N₃O₁₄P₂⁻
Exact Mass: 572.10
Determined: 572.14
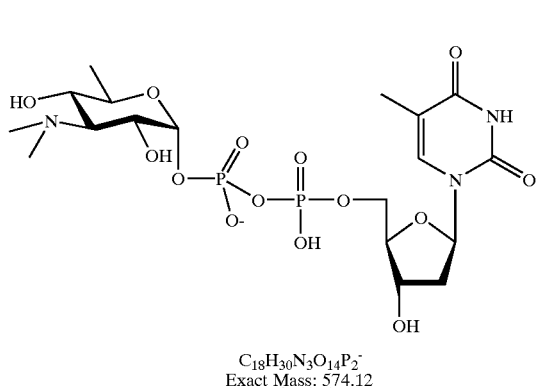
C₁₈H₃₀N₃O₁₄P₂⁻
Exact Mass: 574.12
Determined: 574.12
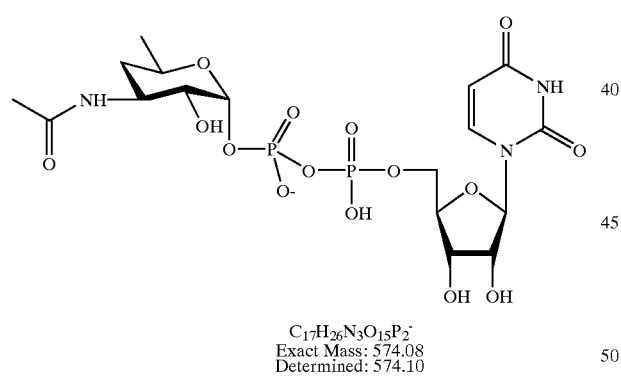
C₁₇H₂₆N₃O₁₅P₂⁻
Exact Mass: 574.08
Determined: 574.10
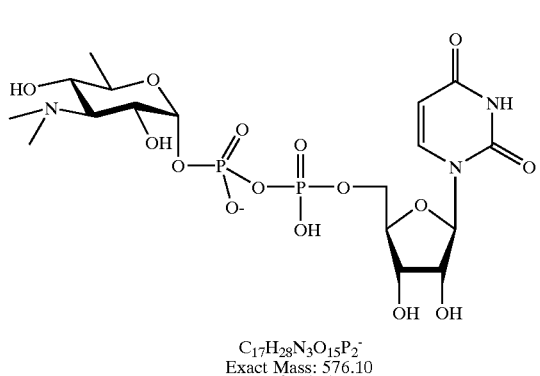
C₁₇H₂₈N₃O₁₅P₂⁻
Exact Mass: 576.10
Determined: 576.03
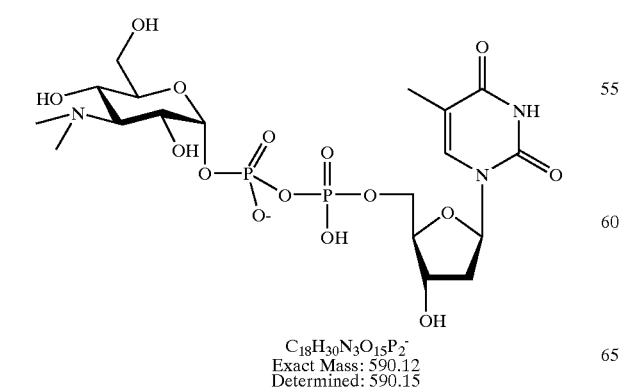
C₁₈H₃₀N₃O₁₅P₂⁻
Exact Mass: 590.12
Determined: 590.15
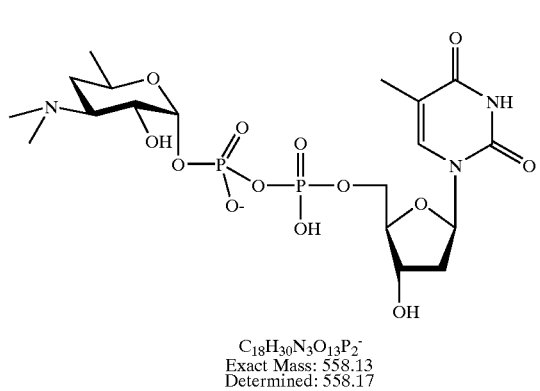
C₁₈H₃₀N₃O₁₃P₂⁻
Exact Mass: 558.13
Determined: 558.17

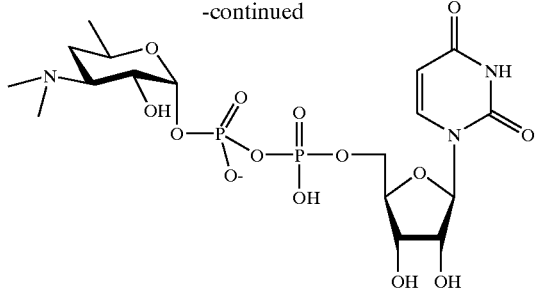

C₁₇H₂₈N₃O₁₄P₂⁻
Exact Mass: 560.10
Determined: 560.15

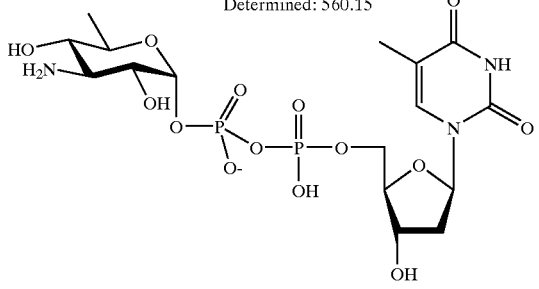

C₁₆H₂₆N₃O₁₄P₂⁻
Exact Mass: 546.09
Determined: 546.05

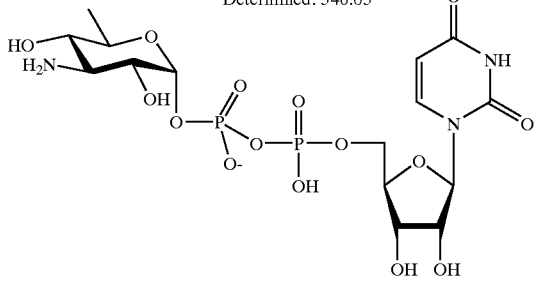

C₁₅H₂₄N₃O₁₅P₂⁻
Exact Mass: 548.07
Determined: 548.13

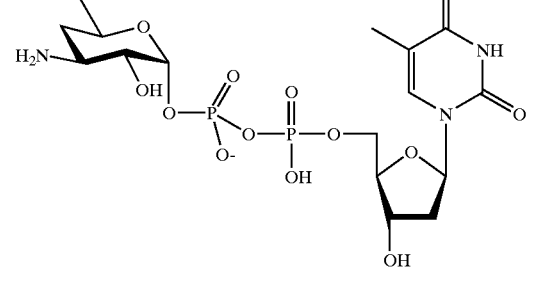

C₁₆H₂₆N₃O₁₃P₂⁻
Exact Mass: 530.09
Determined: 530.04

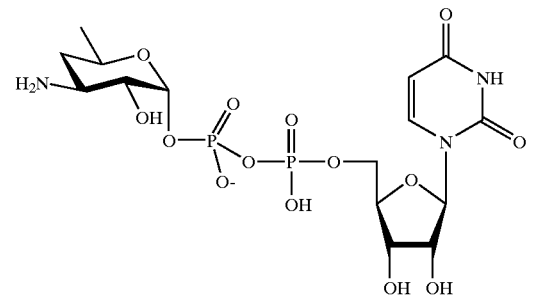

C₁₅H₂₄N₃O₁₄P₂⁻
Exact Mass: 532.07
Determined: 532.10

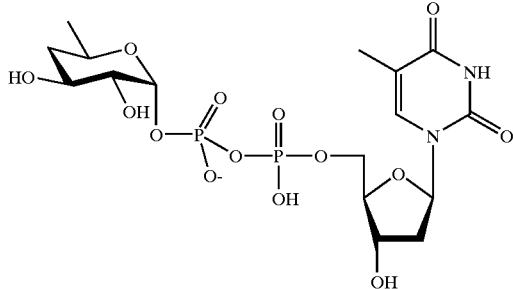

C₁₆H₂₅N₂O₁₄P₂⁻
Exact Mass: 531.08
Determined: 531.07

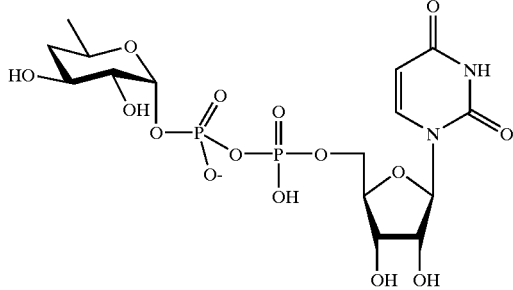

C₁₅H₂₃N₂O₁₅P₂⁻
Exact Mass: 533.06
Determined: 533.09

Methods for synthesizing these and other nucleotide sugars are described in Jiang J. et al., "Expanding the Pyrimidine Diphosphosugar Repertoire: The Chemoenzymatic Synthesis of Amino- and Acetamidoglucopyranosyl Derivatives" *Angew Chem Int Ed Engl* 40(8):1502–1505 (2001); Jiang J. et al., "A General Enzymatic Method for the Synthesis of Natural and 'Unnatural' UDP- and TDP-Nucleotide Sugars," *Journal of the American Chemical Society* 122(28): 6803–6804 (2000); U.S. Provisional Patent Application Ser. No. 60/254,927, U.S. patent application Ser. No. 10/013,542, and International Patent Application PCT/US01/47953, all entitled: "Active-Site Engineering of Nucleotidylyltransferases and General Enzymatic Methods for the Synthesis of Natural and 'Unnatural' UDP- and TDP-Nucleotide Sugars." Each of these references is hereby incorporated by reference in its entirety. Additional novel nucleotide sugars may be synthesized using the general synthetic methods described therein.

Further, additional nucleotide sugars may be synthesized utilizing nucleotidyltransferases that have been mutated to alter or broaden their substrate specificity.

For example, the present inventors discovered the three dimensional structure of and the molecular details of substrate recognition by *Salmonella enterica* LT2 rmlA-encoded α-D-glucopyranosyl phosphate thymidylyltransferase ($E_p$), which catalyzes the conversion of α-D-glucopyranosyl phosphate (Glc-1-P) and dTTP to dTDP-α-D-glucose (TDP-Glc) and pyrophosphate ($PP_i$). The present inventors have used this information to design mutants of Ep having substrate specificity that varies from that of wild type Ep.

In particular, the present inventors have discovered that, in order to alter substrate specificity, it is preferable to mutate nucleotidyltransferases, such as Ep, at one or more amino acids in the active site, the divalent cation binding site, and/or the auxiliary site. More particularly, the present inventors have discovered that it is preferable to mutate $E_p$ at one or more amino acids selected from the group consisting of V173, G147, W224, N112, G175, D111, E162, T201, I200, E199, R195, L89, L89T, L109, Y146 and Y177. Methods for mutating nucleic acids and expressing mutant proteins therefrom are well known in the arts of genetic and protein engineering.

Exemplary nucleotide sugars which may be produced by mutated nucleotidyltransferases and which may be used in methods according to the present invention include, but are not limited to: Thymidine 5'-(6-acetamido-6-deoxy-α-D-glucopyranosyl diphosphate); Uridine 5'-(6-acetamido-6-deoxy-α-D-glucopyranosyl diphosphate); Thymidine 5'-(α-D-glucopyran-6-uronic acid diphosphate); Uridine 5'-(α-D-glucopyran-6-uronic acid diphosphate); Thymidine 5'-(2-acetamido-2-deoxy-α-D-glucopyranosyl diphosphate); Uridine 5'-(2-acetamido-2-deoxy-α-D-glucopyranosyl diphosphate); Thymidine 5'-(4-amino-4,6-dideoxy-α-D-glucopyranosyl diphosphate); Uridine 5'-(4-amino-4,6-dideoxy-α-D-glucopyranosyl diphosphate); Thymidine 5'-(α-D-arabinopyranosyl diphosphate); and Uridine 5'-(α-D-arabinopyranosyl diphosphate).

Methods for producing mutated nucleotidyltransferases and for synthesizing these and other sugars are described in Barton W A, et al., "Structure, mechanism and engineering of a nucleotidylyltransferase as a first step toward glycorandomization," *Nat Struct Biol* 8(6):545–51 (2001); U.S. Provisional Patent Application Ser. No. 60/254,927, U.S. patent application Ser. No. 10/013,542, and International Patent Application PCT/US01/47953, all entitled: "Active-Site Engineering of Nucleotidylyltransferases and General Enzymatic Methods for the Synthesis of Natural and 'Unnatural' UDP- and TDP-Nucleotide Sugars." Each of these references is hereby incorporated by reference in its entirety. Additional mutated nucleotidyltransferases and additional novel nucleotide sugars may be synthesized using the general synthetic methods described therein.

In addition to the great diversity of nucleotide sugars now available, a large number of glycosyltransferases are available. Any known glycosyltransferase may be selected for use in the methods of the present invention. Preferably, glycosyltransferases for use in the present invention are selected from those glycosyltransferases known to be involved in the synthesis of bioactive metabolites. Additionally, glycosyltransferase for use in the methods of the present invention may be produced by expressing the product of a putative glycosyltransferase gene. Such genes are known in the art, and methods for expressing gene products are also known in the art.

In certain embodiments, the glycosyltransferase is selected from the group including, but not limited to, CalB, CalE, CalN, CalU, Gra orfl4, Gra orf5, LanGT1, LanGT2, LanGT3, LanGT4, MtmGI, MtmGII, MtmGTIII, MtmGTIV, NovM, RhlB, Rif orf 7, SnogD, SnogE, SnogZ, UrdGT1a, UrdGT1b, UrdGT1c, UrdGT2, AknK, AknS, DesVII, DnrS, OleG1, OleG2, TylCV, TylMII, TylN, DauH, DnrH, EryBV, EryCIII, Ngt, BgtA, BgtB, BgtC, GftA, GftB, GftC, GftD, GftE, Gp1-1, Gp1-2, RtfA, AveBI, BlmE, BlmF, MgtA, NysD1, OleD, OleI, SpcF, SpcG, StrH, Ugt51B1, Ugt51C1, UGT52, UgtA, UgtB, UgtC, UgtD and homologs thereof. See, e.g., U.S. Ser. Nos. 09/457,045; 09/724,797; Thorson, J. S. et al. "Nature's Carbohydrate Chemists: The Enzymatic Glycosylation of Bioactive Bacterial Metabolites," *Curr. Org. Chem.* 5: 139–167 (2001); Weymouth-Wilson, A. C. "The Role of Carbohydrates in Biologically Active Natural Products," *Nat. Prod. Rep.* 14: 99–110 (1997).

When one or more moieties capable of being glycosylated and a diverse pool of NDP-sugars are incubated in under appropriate conditions in the presence of a glycosyltransferase, a diverse library of glycorandomized structures is produced. Incubating the resultant glycosylated entities one or more additional times in the presence of the same or different glycosyltransferase(s) and a pool of the same or different sugars results in a library of glycorandomized structures that becomes more diverse and complex with each glycosylation incubation.

In this manner, coupled with the presented $E_p$-catalyzed production of NDP-sugar donor libraries and the appropriate aglycon, or moiety capable of being glycosylated, the flexibility of wild-type glycosyltransferases in secondary metabolism can be used to rapidly generate a diverse library of "glycorandomized" structures, in combinatorial fashion, based upon a particular natural product scaffold. Moieties capable of being glycosylated may be referred to as "aglycons." However, when the aglycon of a specific biomolecule is referred to (e.g., the aglycon of anthracyclines), the specific aglycon of that specific biomolecule is meant.

Using methods of combinatorial chemistry, glycosyltransferase(s) are incubated with a pool of nucleotide sugar substrates and a pool of entities capable of being glycosylated under conditions favoring the transfer by the glycosyltransferase of the glycosyl groups from the nucleotide sugar substrates to the entities capable of being glycosylated. General appropriate conditions are known in the art. Appropriate conditions may vary from one particular enzyme to another, and optimal conditions for any particular enzyme may be determine using methods known in the art.

The incubation may be carried out with one or more glycosyltransferases. Likewise, the pool of nucleotide sugars may comprise one or more sugars. Preferably, the pool of sugars comprises different nucleotidyl sugars. More preferably, the pool of sugars comprises a highly diverse population of nucleotidyl sugars. The pool of sugars may comprise known nucleotidyl sugars and/or novel nucleotidyl sugars. When it is desired to use novel nucleotidyl sugars, such sugars may be made by exploiting the promiscuity of nucleotidyltransferases by employing the methods described in Jiang, J. et al. (2000); Jiang J. et al. (2001); Barton W. A., et al., "Structure, Mechanism and Active-Site Engineering of a Nucleotidylyltransferase: The First Step in the Glycorandomization of Natural Product-Based Metabolites," *Nature Structural Biology* (2001), manuscript in press; and U.S. Ser. No. 60/254,927.

The incubation may be carried out with one or more entity capable of being glycosylated. Entities capable of being glycosylated may be selected from natural and synthetic aglycons, natural product metabolites, oligosaccharides, proteins, and peptides. Entities capable of being glycosylated may also be selected from the aglycons of bioactive anthracyclines, angucyclines, nonribosomal peptides (such as vancomycin), macrolides, enediynes, indolocarbazoles, pluramycins, aurelolic acids, orthosomycins, aminoglycosides, coumarins, bleomycins, amicetins, polyenes, benzoisochromanequinones, angucyclines, steroids, lipids, polyketides, oligosaccharides, peptides, proteins, other numerous classes of bioactive metabolites, and hybrids consisting of one or more of these components.

Entities capable of being glycosylated include entities that are already glycosylated, whether by methods of the present invention, by other synthetic or biosynthetic methods, or naturally occurring. Additional glycosyl groups may be attached to a previously attached glycosyl group in order to form a saccharide chain. Additional glycosyl groups may also or alternatively be attached to the original entity capable of being glycosylated, e.g., the aglycon.

The same glycosyltransferase may be used in repeated cycles of glycosylation of a pool of entities capable of being glycosylated. However, preferably, different glycosyltransferases are used in repeated cycles of glycosylation. In this manner, entities that have been glycosylated according to the methods of the present invention may be subjected to repeated cycles of incubation with glycosyltransferases and pools of sugars until a population of the desired type and size of glycosylated entities is achieved. Preferably, the population of glycosylated entities produced is highly diverse. Also preferably, the pool of glycosylated entities produced comprises novel compounds. Most preferably, the pool of glycosylated entities comprises compounds with novel, enhanced, and/or therapeutically useful biological activity.

Two novel novobiocin (designated Nov-1 and Nov-2) derivatives and six novel erythromycin (designated Ery-1–Ery-6) analogs were produced using the methods of the present invention. By exposing these novel compounds to repeated cycles of glycosylation, a large library of diverse novel compounds may be produced.

The present invention will now be illustrated by the following examples, which show how certain specific representative embodiments of the compounds and methods of the present invention, the compounds, intermediates, process steps, and the like being understood as examples that are intended to be illustrative only. In particular, the invention is not intended to be limited to the conditions, order of the steps and the like specifically recited herein. Rather, the Examples are intended to be illustrative only.

EXAMPLES

Sugars

For all Examples, the sugars tested included or includes: UDP xylose (commercially available); Thymidine 5'-($\alpha$-D-glucopyranosyl diphosphate); Uridine 5'-($\alpha$-D-glucopyranosyl diphosphate); Thymidine 5'-(2-deoxy-$\alpha$-D-glucopyranosyl diphosphate); Uridine 5'-(2-deoxy-$\alpha$-D-glucopyranosyl diphosphate); Thymidine 5'-(3-deoxy-$\alpha$-D-glucopyranosyl diphosphate); Uridine 5'-(3-deoxy-$\alpha$-D-glucopyranosyl diphosphate); Thymidine 5'-(4-deoxy-$\alpha$-D-glucopyranosyl diphosphate); Uridine 5'-(4-deoxy-$\alpha$-D-glucopyranosyl diphosphate); Thymidine 5'-(6-deoxy-$\alpha$-D-glucopyranosyl diphosphate); Uridine 5'-(6-deoxy-$\alpha$-D-glucopyranosyl diphosphate); Thymidine 5'-($\alpha$-D-mannopyranosyl diphosphate); Uridine 5'-($\alpha$-D-mannopyranosyl diphosphate); Thymidine 5'-($\alpha$-D-galactopyranosyl diphosphate); Uridine 5'-($\alpha$-D-galactopyranosyl diphosphate); Thymidine 5'-($\alpha$-D-allopyranosyl diphosphate); Thymidine 5'-($\alpha$-D-altropyranosyl diphosphate); Thymidine 5'-(2-amino-2-deoxy-$\alpha$-D-glucopyranosyl diphosphate); Uridine 5'-(2-amino-2-deoxy-$\alpha$-D-glucopyranosyl diphosphate); Thymidine 5'-(3-amino-3-deoxy-$\alpha$-D-glucopyranosyl diphosphate); Uridine 5'-(3-amino-3-deoxy-$\alpha$-D-glucopyranosyl diphosphate); Thymidine 5'-(4-amino-4-deoxy-$\alpha$-D-glucopyranosyl diphosphate); Uridine 5'-(4-amino-4-deoxy-$\alpha$-D-glucopyranosyl diphosphate); Thymidine 5'-(6-amino-6-deoxy-$\alpha$-D-glucopyranosyl diphosphate); Uridine 5'-(6-amino-6-deoxy-$\alpha$-D-glucopyranosyl diphosphate); Thymidine 5'-(4-amino-4,6-dideoxy-$\alpha$-D-glucopyranosyl diphosphate); Uridine 5'-(4-amino-4,6-dideoxy-$\alpha$-D-glucopyranosyl diphosphate); Thymidine 5'-(2-acetamido-2-deoxy-$\alpha$-D-glucopyranosyl diphosphate); Uridine 5'-(2-acetamido-2-deoxy-$\alpha$-D-glucopyranosyl diphosphate); Thymidine 5'-(3-acetamido-3-deoxy-$\alpha$-D-glucopyranosyl diphosphate); and Uridine 5'-(6-acetamido-6-deoxy-$\alpha$-D-glucopyranosyl diphosphate).

Methods for making these and other sugars are described in Barton W A, et al., "Structure, mechanism and engineering of a nucleotidylyltransferase as a first step toward glycorandomization," *Nat Struct Biol* 8(6):545–51 (2001); Jiang J, et al., "Expanding the Pyrimidine Diphosphosugar Repertoire: The Chemoenzymatic Synthesis of Amino- and Acetamidoglucopyranosyl Derivatives" *Angew Chem Int Ed Engl* 40(8):1502–1505 (2001); Jiang J, et al., "A General Enzymatic Method for the Synthesis of Natural and 'Unnatural' UDP- and TDP-Nucleotide Sugars," *Journal of the American Chemical Society* 122(28): 6803–6804 (2000); U.S. Provisional Patent Application Ser. No. 60/254,927, U.S. patent application Ser. No. 10/013,542, and International Patent Application PCT/US01/47953, all entitled: "Active-Site Engineering of Nucleotidylyltransferases and General Enzymatic Methods for the Synthesis of Natural and 'Unnatural' UDP- and TDP-Nucleotide Sugars." Each of these references is hereby incorporated by reference in its entirety.

Example 1

Novel Macrolide Antibiotics 2.5 mM nucleotide sugar, 2 mM aglycon 17, and 10 $\mu$g of glycosyltransferase EryCIII in 50 mM potassium phosphate buffer (pH 8.0) was incubated at 37° C. for 12 hr, then concentrated via lyopholization.

The resultant mixture was analyzed by HPLC ($C_{18}$, 25% $CH_3CN$/20 mM potassium phosphate, pH 9.0 for the first 10 min followed by an increase to 40% $CH_3CN$ for an additional 25 min; erythronolides observed at 205 nm). Under these conditions, the retention times for the standards aglycon 17 and erythromycin $A_1$ were 11 min and 25 min, respectively. New peaks, in comparison to the appropriate controls, were observed in the presence of: thymidine 5'-(2-deoxy-$\alpha$-D-glucopyranosyl diphosphate) (to give Ery-1 with a retention time of 15 min); thymidine 5'-(2-amino-2-deoxy-$\alpha$-D-glucopyranosyl diphosphate) (to give Ery-2 with a retention time of 13 min); thymidine 5'-(3-deoxy-$\alpha$-D-glucopyranosyl diphosphate) (to give Ery-3 with a retention time of 15 min); thymidine 5'-(4-deoxy-$\alpha$-D-glucopyranosyl diphosphate) (to give Ery-4 with a retention time of 15 min); thymidine 5'-(6-deoxy-$\alpha$-D-glucopyranosyl diphosphate) (to give Ery-5 with a retention time of 15 min); and thymidine 5'-($\alpha$-D-galactopyranosyl diphosphate) (to give Ery-6 with a retention time of 16 min). These peaks were isolated and characterized by HRMS, confirming the identity of the compounds presented in FIG. 3. The presented stereo- and regiochemistry of these structures is based upon the known reaction catalyzed by EryCIII.

The aglycon 17 can be obtained from *Saccharopolyspoar erythrea*, which produces the compound naturally. In addition, genetic manipulations can be made which result in *S. erythrea* which make greater quantities of this aglycon. The nucleotide sugar library examined (see above under "Sugars") contained a few commercially available analogs, but was comprised primarily of synthetically if generated derivatives. Jiang, J. et al (2000); Jiang J. et al. (2001); Barton W. A., et al., "Structure, Mechanism and Active-Site Engineering of a Nucleotidylyltransferase: The First Step in the Glycorandomization of Natural Product-Based Metabolites," *Nature Structural Biology* (2001), manuscript in press; and U.S. Ser. No. 60/254,927. Each sugar was presented individually in a reaction separate from other sugars.

Figure 3:
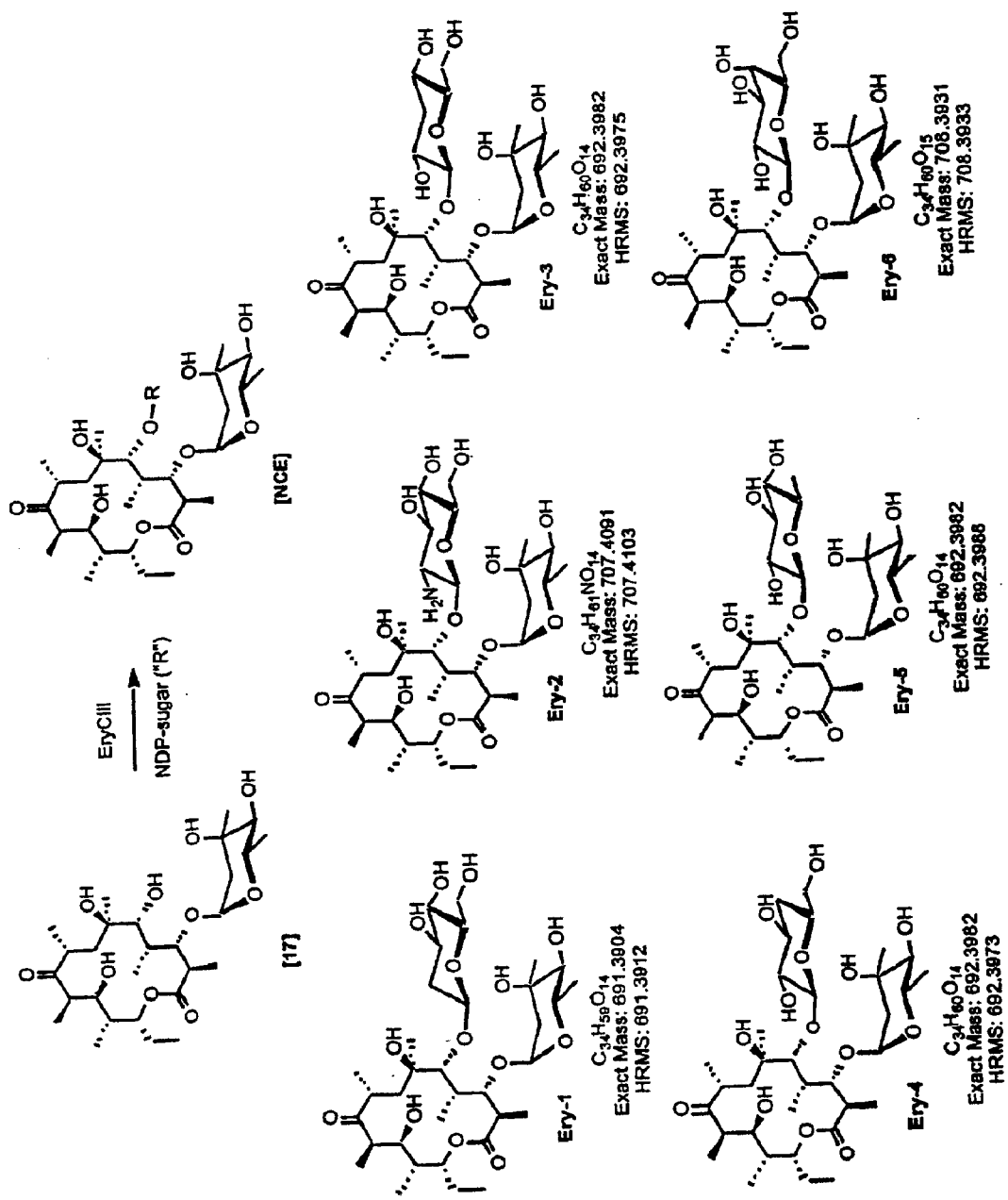
FIG. 3 provides chemical structures for new chemical entities (NCEs) Ery-1, Ery-2, Ery-3, Ery-4, Ery-5, and Ery-6.

In FIG. 3, the "R" designates the sugar portion of the NDP-sugar which is transferred by EryCIII to aglycon 17 to generate the new compounds (designated New Chemical Entity in FIG. 3). The gene encoding EryCIII (eryCIII, accessions AAB84072 and CAA74710; Stauton, J. et al. *Chem. Rev.* 97: 2611 (1997); Summers, R. G., et al. *Microbiol.* 143: 3251 (1997)) was PCR amplified directly from *S. erythrea* genomic DNA, isolated from a strain purchased from ATCC, and expressed as a C-terminus His-tag fusion protein. EryCIII was subsequently overexpressed in *E. coli*, partially purified using a nickel affinity column and used as a fresh preparation in the assays.

Example 2

Novel Coumarin Antibiotics 2.5 mM nucleotide sugar, 2 mM aglycon 20, and 10 μg of glycosyltransferase NovM in 50 mM potassium phosphate buffer (pH 8.0) was incubated at 37° C. for 12 hr, then concentrated via lyopholization.

The resultant mixture was analyzed by HPLC ($C_{18}$, 70–80% MeOH/0.1% TFA, novobiocin analogs visualized at 305 nm). Under these conditions, the retention times for the standards aglycon 20 and novobiocin (4) were 21 min and 23 min, respectively. New peaks, in comparison to the appropriate controls, were observed in the presence of: thymidine or uridine 5'-(6-deoxy-α-D-glucopyranosyl diphosphate) (to give Nov-1 with a retention time of 17 min); and thymidine 5'-(α-D-xylopyranosyl diphosphate) (to give Nov-2 with a retention time of 16 min). These peaks were isolated and characterized by HRMS, confirming the identity of the compounds presented in FIG. 4. The presented stereo- and regiochemistry of these structures is based upon the known reaction catalyzed by NovM.

The aglycon 20 was synthesized via the chemical hydrolysis of commercially available novobiocin. The nucleotide sugar library examined (see above under "Sugars") contained a few commercially available analogs, but was comprised primarily of synthetically generated derivatives. Jiang, J. et al. (2000); Jiang J. et al. (2001); Barton W. A., et al., "Structure, Mechanism and Active-Site Engineering of a Nucleotidylyltransferase: The First Step in the Glycorandomization of Natural Product-Based Metabolites," *Nature Structural Biology* (2001), manuscript in press; and U.S. Ser. No. 60/254,927. Each sugar was presented individually in a reaction separate from other sugars.

Figure 4:
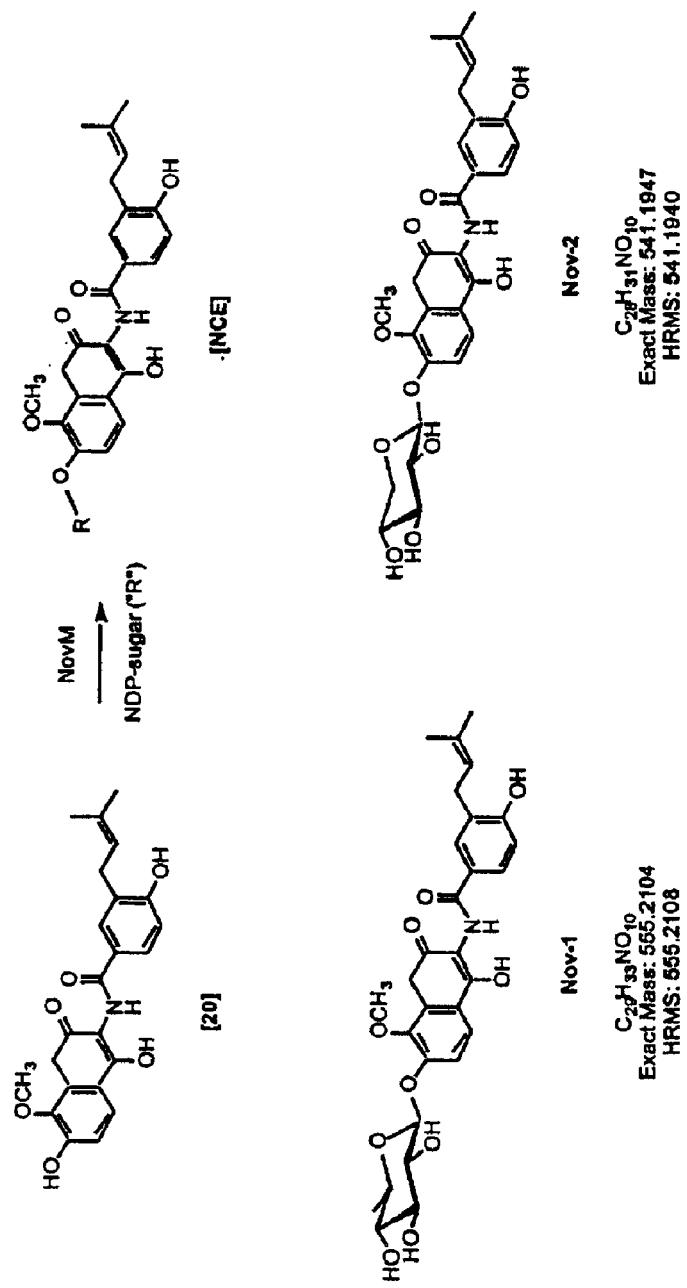
FIG. 4 provides chemical structures for new chemical entities (NCEs) Nov-1 and Nov-2.

In FIG. 4, the "R" designates the sugar portion of the NDP-sugar which is transferred by NovM to aglycon 20 to generate the new compounds (designated New Chemical Entity in FIG. 4). The gene encoding NovM (novM, accession AAF67506) was PCR amplified directly from *S. spheroides* genomic DNA, isolated from a strain purchased from ATCC, and expressed as a C-terminus His-tag fusion protein. NovM was subsequently overexpressed in *E. coli*, partially purified using a nickel affinity column and used as a fresh preparation in the assays.

Example 3

Generation of Larger Combinatorial Libraries 2 mM each of newly generated Ery-1 through Ery-6 are incubated at 37° C. for 12 hr with 2.5 mM nucleotide sugar and 10 μg of glycosyltransferase MegD1 (the next glycosyltransferase in the megalomicin cascade). In the presence of a pool of 20 nucleotide sugars, an anticipated 120 NCE's (6×20) are generated.

The resultant mixture is analyzed by HPLC ($C_{18}$, 70–80% MeOH/0.1% TFA, erythronolides observed at 205 nm). Novel compounds are identified. New peaks are isolated and characterized by HRMS. Stereo- and regiochemistry of the novel erythronolides are determined based upon the known reaction catalyzed by MegD1.

The nucleotide sugar library examined (see above under "Sugars") contains a few commercially available analogs, but is comprised primarily of synthetically generated derivatives. Jiang, J. et al. (2000); Jiang J. et al. (2001); Barton W. A., et al., "Structure, Mechanism and Active-Site Engineering of a Nucleotidylyltransferase: The First Step in the Glycorandomization of Natural Product-Based Metabolites," *Nature Structural Biology* (2001), manuscript in press; and U.S. Ser. No. 60/254,927. Each sugar is presented individually in a reaction separate from other sugars.

Example 4

Novel Non-Ribosomal Peptides 3 mM each of aglycon from vancomycin, teicoplanin or chloroeremomycin are incubated at 37° C. for 12 hr with 6 mM nucleotide sugars and 10 μg of glycosyltransferase (GtfA-E from *Amycolatopis orientalis* strains, accession AAB49299, Solenberg, P. J. et al, *Chem. Biol.* 4: 195 (1997)). Products from the first glycosylation are then used as the aglycon for the next glycosyltransferase. In the presence of a pool of 5 glycosyltransferases, 3 aglycons and 20 nucleotide sugars, an anticipated 8800 NCE's ([20×20× 20]+[20×20]+[20×20]=8800) are generated.

The resultant mixture is analyzed by HPLC ($C_{18}$, 0–40% $CH_3CN$/0.1% TFA, erythronolides observed at 285 nm). Novel compounds are identified. New peaks are isolated and characterized by HRMS. Stereo- and regiochemistry of the novel non-ribosomal peptides are determined based upon the known reaction catalyzed by GtfA-E.

The nucleotide sugar library examined (see above under "Sugars") contains a few commercially available analogs, but is comprised primarily of synthetically generated derivatives. Jiang, J. et al. (2000); Jiang J. et al. (2001); Barton W. A., et al., "Structure, Mechanism and Active-Site Engineering of a Nucleotidylyltransferase: The First Step in the Glycorandomization of Natural Product-Based Metabolites," *Nature Structural Biology* (2001), manuscript in press; and U.S. Ser. No. 60/254,927. Each sugar is presented individually in a reaction separate from other sugars.

Example 5

Figure 5:
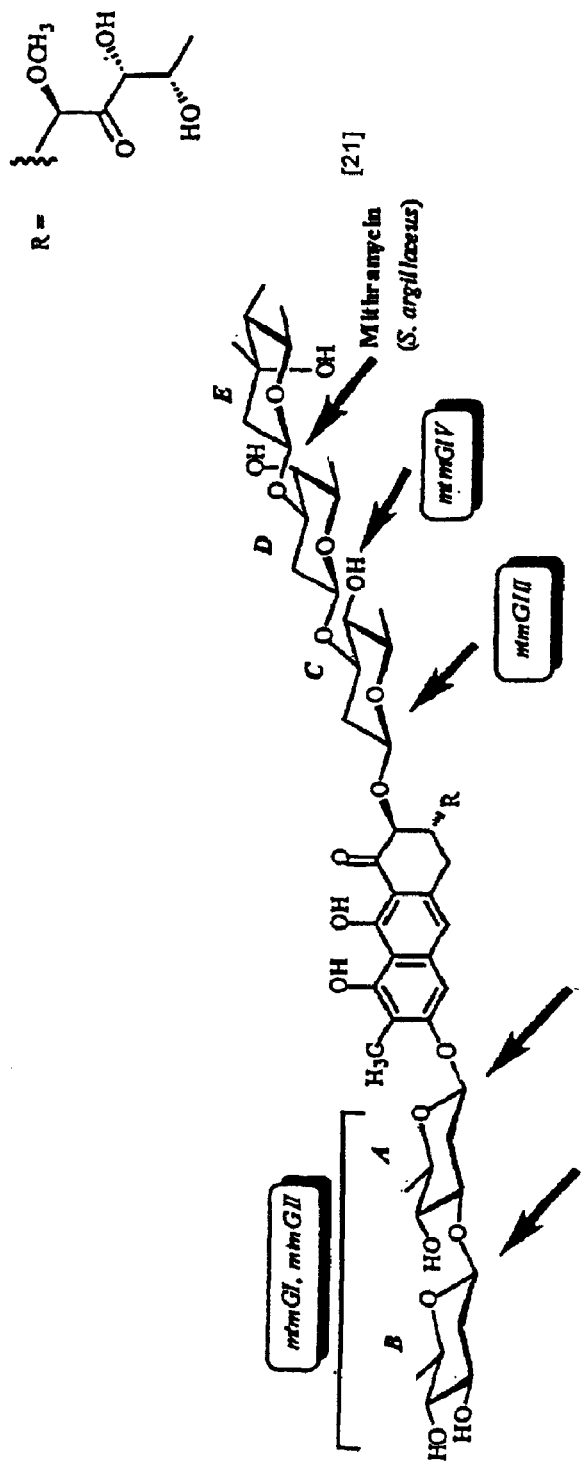
FIG. 5 provides a chemical structure for antitumor agent mithramycin.

Novel Aureolic Acids 2 mM of aglycon from the known antitumor agent mithramycin (FIG. 5, 21; Thorson, J. S. et al. (2001)) is incubated at 37° C. for 12 hr with 2.5 mM nucleotide sugars and 10 μg of glycosyltransferase (MtmI, encoded by mtmGI cloned from *Streptomyces argillaceus* (accession AAC64927)). Products from the first glycosylation are then used as the aglycon for the next glycosyltransferase, (MtmII, encoded by mtmGII cloned from *Streptomyces argillaceus* (accession AAC64927)). Products from the second glycosylation are then used as the aglycon for the third glycosyltransferase, (MtmIII, encoded by mtmGIII cloned from *Streptomyces argillaceus* (accession AAC64927)). Products from the third glycosylation are then used as the aglycon for the fourth glycosyltransferase, (MtmIV, encoded by mtmGIV cloned from *Streptomyces argillaceus* (accession AAC64927)).

The nucleotide sugar library examined (see above under "Sugars") contains a few commercially available analogs, but is comprised primarily of synthetically generated derivatives. Jiang, J. et al. (2000); Jiang J. et al. (2001); Barton W. A., et al., "Structure, Mechanism and Active-Site Engineering of a Nucleotidylyltransferase: The First Step in the Glycorandomization of Natural Product-Based Metabolites," *Nature Structural Biology* (2001), manuscript in press; and U.S. Ser. No. 60/254,927. Each sugar is presented individually in a reaction separate from other sugars.

For each of the glycosyltransferases, 20 reactions are carried out, each with one of 20 different sugar phosphates). The anticipated library size will be the result of combining 20 different sugars at 5 different positions (each individually attached by the appropriate glycosyltransferase) on mithramycin to give $20^5$, or >3 million distinct mithramycin-based variants.

The resultant mixture is analyzed by HPLC ($C_{18}$, 0–40% $CH_3CN/0.1\%$ TFA, erythronolides observed at 285 nm). Novel compounds are identified. New peaks are isolated and characterized by HRMS. Stereo- and regiochemistry of the novel aureolic acids are determined based upon the known reactions catalyzed by MtmI-MtmIV.

I claim:

1. A method of preparing a glycosylated compound comprising steps of:
   (a) preparing a nucleotide sugar by combining an NTP and at least one sugar phosphate in the presence of at least one nucleotidyltransferase Ep mutated at one or more amino acids selected from the group consisting of V173, G147, W224, N112, G175, D111, E162, T201, I200, E199, R195, L89, L89T, L109, Y146 and Y177;
   (b) combining the nucleotide sugar prepared in step (a) with a glycosyltransferase and a moiety capable of being glycosylated, thereby producing at least one glycosylated compound; and
   (c) recovering the glycosylated compound.

2. The method of claim 1, further wherein the method is carried out in vitro.

3. The method of claim 1, further wherein the nucleotide sugars is a nucleotide diphospho sugar.

4. The method of claim 1, further wherein the nucleotide sugars is selected from the group consisting of Thymidine 5'-(α-D-glucopyranosyl diphosphate); Uridine 5'-(α-D-glucopyranosyl diphosphate); Thymidine 5'-(2-deoxy-α-D-glucopyranosyl diphosphate); Uridine 5'-(2-deoxy-α-D-glucopyranosyl diphosphate); Thymidine 5'-(3-deoxy-α-D-glucopyranosyl diphosphate); Uridine 5'-(3-deoxy-α-D-glucopyranosyl diphosphate); Thymidine 5'-(4-deoxy-α-D-glucopyranosyl diphosphate); Uridine 5'-(4-deoxy-α-D-glucopyranosyl diphosphate); Thymidine 5'-(6-deoxy-α-D-glucopyranosyl diphosphate); Uridine 5'-(6-deoxy-α-D-glucopyranosyl diphosphate); Thymidine 5'-(α-D-mannopyranosyl diphosphate); Uridine 5'-(α-D-mannopyranosyl diphosphate); Thymidine 5'-(α-D-galactopyranosyl diphosphate); Uridine 5'-(α-D-galactopyranosyl diphosphate); Thymidine 5'-(α-D-allopyranosyl diphosphate); Thymidine 5'-(α-D-altropyranosyl diphosphate); Uridine 5'-(α-D-allopyranosyl diphosphate); Uridine 5'-(α-D-altropyranosyl diphosphate); Thymidine 5'-(α-D-gulopyranosyl diphosphate); Uridine 5'-(α-D-gulopyranosyl diphosphate); Thymidine 5'-(α-D-idopyranosyl diphosphate); Uridine 5'-(α-D-idopyranos-yl diphosphate); Thymidine 5'-(α-D-talopyranosyl diphosphate); Uridine 5'-(α-D-talopyranosyl diphosphate); Thymidine 5'-(6-amino-6-deoxy-α-D-glucopyranosyl diphosphate); Uridine 5'-(6-amino-6-deoxy-α-D-glucopyranosyl diphosphate); Thymidine 5'-(4-amino-4-deoxy-α-D-glucopyranosyl diphosphate); Uridine 5'-(4-amino-4-deoxy-α-D-glucopyranosyl diphosphate); Thymidine 5'-(3-amino-3-deoxy-α-D-glucopyranosyl diphosphate); Uridine 5'-(3-amino-3-deoxy-α-D-glucopyranosyl diphosphate); Thymidine 5'-(2-amino-2-deoxy-α-D-glucopyranosyl diphosphate); Uridine 5'-(2-amino-2-deoxy-α-D-glucopyranosyl diphosphate); Thymidine 5'-(6-acetamido-6-deoxy-α-D-glucopyranosyl diphosphate); Uridine 5'-(6-acetamido-6-deoxy-α-D-glucopyranosyl diphosphate); Thymidine 5'-(4-acetamido-4-deoxy-α-D-glucopyranosyl diphosphate); Uridine 5'-(4-acetamido-4-deoxy-α-D-glucopyranosyl diphosphate); Thymidine 5'-(3-acetamido-3-deoxy-α-D-glucopyranosyl diphosphate); Uridine 5'-(3-acetamido-3-deoxy-α-D-glucopyranosyl diphosphate); Thymidine 5'-(2-acetamido-2-deoxy-α-D-glucopyranosyl diphosphate); Uridine 5'-(2-acetamido-2-deoxy-α-D-glucopyranosyl diphosphate); Thymidine 5'-(4-amino-4,6-dideoxy-α-D-glucopyranosyl diphosphate); Uridine 5'-(4-amino-4,6-dideoxy-α-D-glucopyranosyl diphosphate); Thymidine 5'-(α-D-glucopyran-6-uronic acid diphosphate); Uridine 5'-(α-D-glucopyran-6-uronic acid diphosphate); Thymidine 5'-(α-D-arabinopyranosyl diphosphate); Uridine 5'-(α-D-arabinopyranosyl diphosphate); and

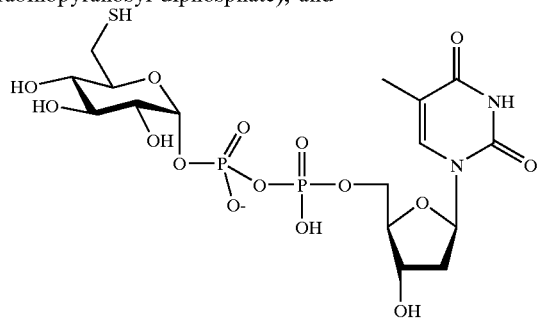

$C_{16}H_{25}N_2O_{15}P_2S^-$
Exact Mass: 579.05
Determined: 579.06

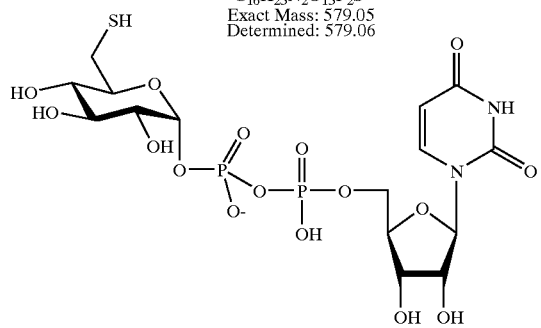

$C_{15}H_{23}N_2O_{16}P_2S^-$
Exact Mass: 581.02
Determined: 581.02

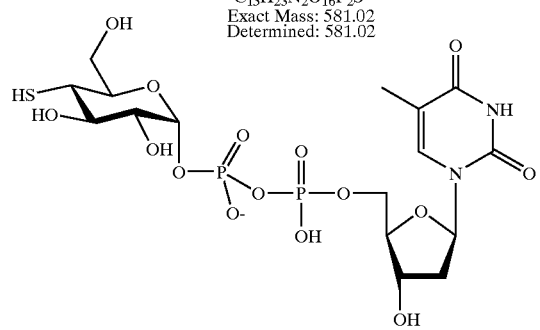

$C_{16}H_{25}N_2O_{15}P_2S^-$
Exact Mass: 579.05
Determined: 579.08

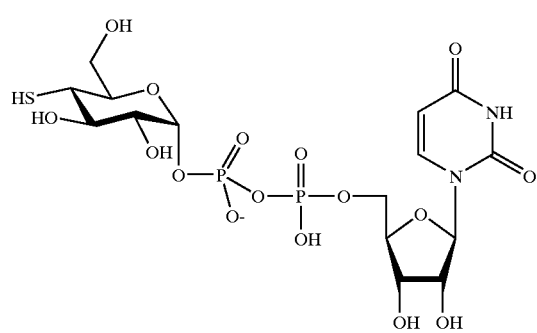
C$_{15}$H$_{23}$N$_2$O$_{16}$P$_2$S$^-$
Exact Mass: 581.02
Determined: 581.01
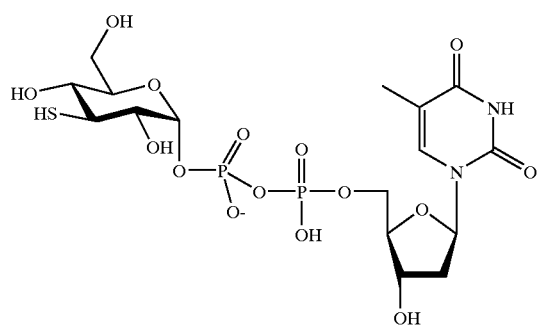
C$_{16}$H$_{25}$N$_2$O$_{15}$P$_2$S$^-$
Exact Mass: 579.05
Determined: 579.02
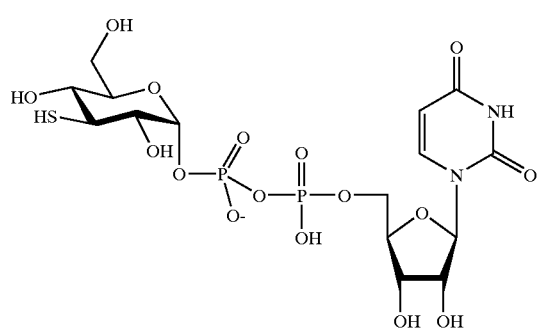
C$_{15}$H$_{23}$N$_2$O$_{16}$P$_2$S$^-$
Exact Mass: 581.02
Determined: 581.05
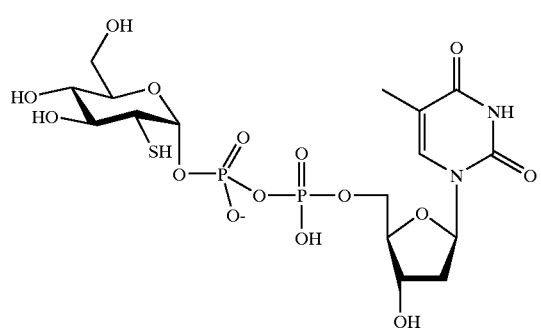
C$_{16}$H$_{25}$N$_2$O$_{15}$P$_2$S$^-$
Exact Mass: 579.05
Determined: 579.10
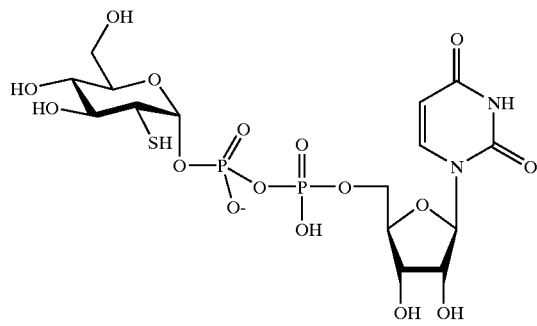
C$_{15}$H$_{23}$N$_2$O$_{16}$P$_2$S$^-$
Exact Mass: 581.02
Determined: 581.08
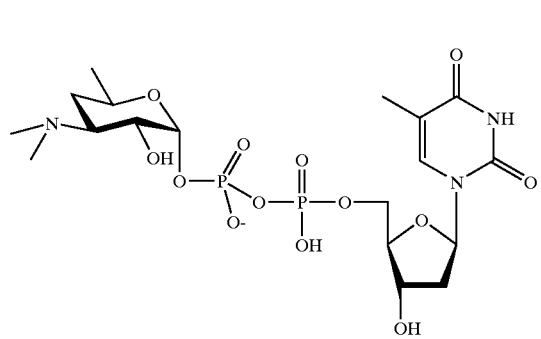
C$_{18}$H$_{30}$N$_3$O$_{13}$P$_2^-$
Exact Mass: 558.13
Determined: 558.17
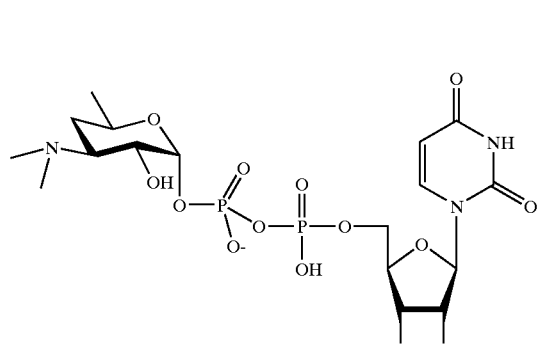
C$_{17}$H$_{28}$N$_3$O$_{14}$P$_2^-$
Exact Mass: 560.10
Determined: 560.15
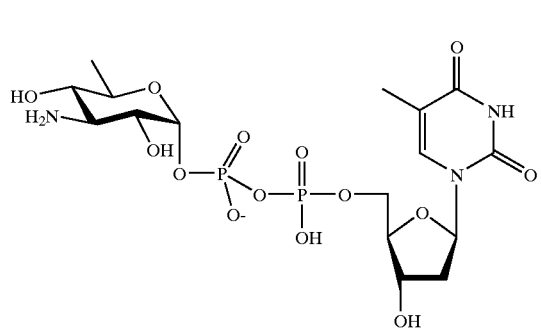
C$_{16}$H$_{26}$N$_3$O$_{14}$P$_2^-$
Exact Mass: 546.09
Determined: 546.05

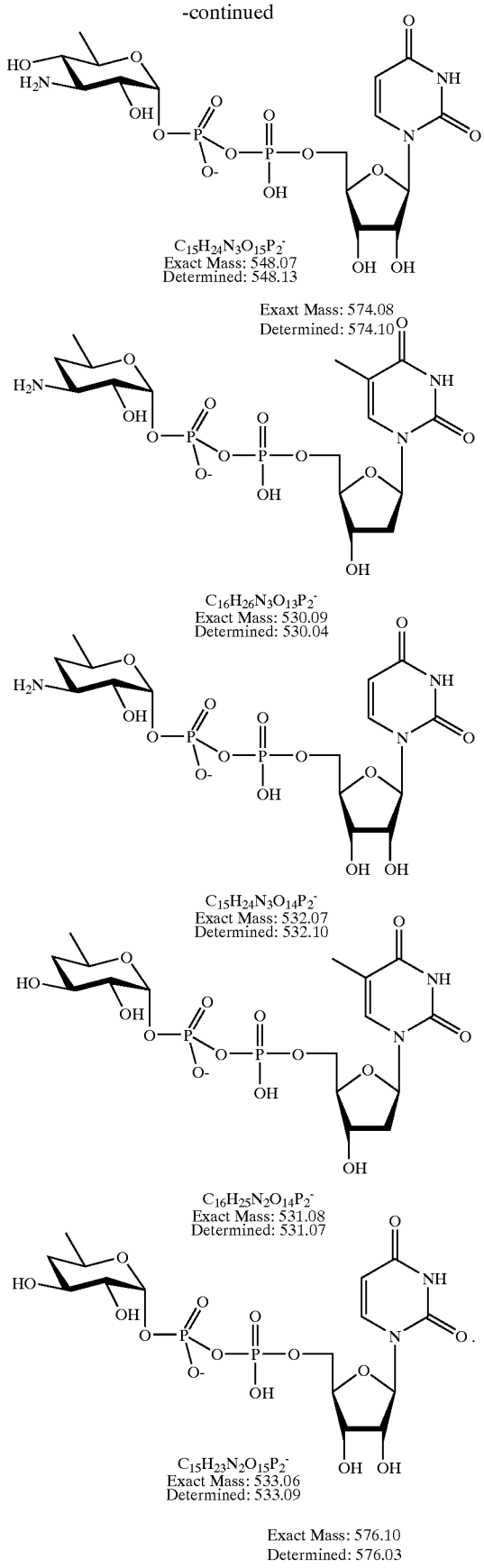

5. The method of claim 1, further wherein more than one nucleotide sugar is incubated with the moiety capable of being glycosylated in the presence of the glycosyltransferase.

6. The method of claim 1, further wherein more than one glycosylated compound is produced in a single reaction vessel.

7. The method of claim 1, further wherein a diverse population of glycosylated compounds is produced.

8. The method of claim 1, further wherein the moiety capable of being glycosylated is selected from the group consisting of natural and synthetic metabolites, pyran rings, furan rings, enediynes, anthracyclines, angucyclines, aureolic acids, orthosomycins, macrolides, aminoglycosides, non-ribosomal peptides, polyenes, steroids, lipids, indolocarbazoles, bleomycins, amicetins, benzoisochromanequinones coumarins, polyketides, pluramycins, aminoglycosides, oligosaccharides, peptides, and proteins.

9. The method of claim 1, further wherein the moiety capable of being glycosylated is selected from the group consisting of aglycons of bioactive anthracyclines, angucyclines, nonribosomal peptides, macrolides, enediynes, indolocarbazoles, pluramycins, aurelolic acids, orthosomycins, aminoglycosides, coumarins, bleomycins, amicetins, polyenes, benzoisochromanequinones, and angucyclines.

10. The method of claim 1, further wherein the moiety capable of being glycosylated is selected from the group consisting of enediynes, anthracyclines, angucyclines, aureolic acids, orthosomycins, macrolides, aminoglycosides, non-ribosomal peptides, polyenes, steroids, lipids, indolocarbazoles, bleomycins, amicetins, benzoisochromanequinones coumarins, polyketides, pluramycins, aminoglycosides, oligosaccharides, peptides, and proteins.

11. The method of claim 1, further wherein the moiety capable of being glycosylated is selected from the group consisting of aglycons of bioactive anthracyclines, angucyclines, nonribosomal peptides, macrolides, enediynes, indolocarbazoles, pluramycins, aurelolic acids, orthosomycins, aminoglycosides, coumarins, bleomycins, amicetins, polyenes, benzoisochromanequinones, and angucyclines.

12. The method of claim 1, further wherein more than one moiety capable of being glycosylated is incubated with the at least one first nucleotide sugar in the presence of the at least one first glycosyltransferase.

13. The method of claim 1, further wherein at least one of the at least one moieties capable of being glycosylated comprises at least one glycosyl group.

14. The method of claim 1, further wherein at least one of the at least one first glycosyltransferase is selected from the group consisting of CalB, CalE, CalN, CalU, Gra orfl4, Gra orf5, LanGT1, LanGT2, LanGT3, LanGT4, MtmGI, MtmGII, MtmGTIII, MtmGTIV, NovM, RhlB, Rif orf 7, SnogD, SnogE, SnogZ, UrdGT1a, UrdGT1b, UrdGT1c, UrdGT2, AknK, AknS, DesVII, DnrS, OleG1, OleG2, TylCV, TylMII, TylN, DauH, DnrH, EryBV, EryCIII, Ngt, BgtA, BgtB, BgtC, GftA, GftB, GftC, GftD, GftE, Gp1-1, Gp1-2, RtfA, AveBI, BlmE, BlmF, MgtA, NysD1, OleD, OleI, SpcF, SpcG, StrH, Ugt51B1, Ugt51C1, UGT52, UgtA, UgtB, UgtC, UgtD and homologs thereof.

15. The method of claim 1, further wherein the at least one moiety capable of being glycosylated is incubated with the at least one novel nucleotide sugar in the presence more than one glycosyltransferase.

16. A method comprising incubating at least one glycosylated compound produced by the method of claim 1 that is capable of being glycosylated with and at least one second nucleotide sugar in the presence of at least one second glycosyltransferase to produce at least one twice-glycosylated compound having at least a first and a second glycosyl attachment.

17. The method of claim 16, further wherein the first and second glycosyl attachments are the same.

18. The method of claim 16, further wherein the first and second glycosyl attachments are different.

19. The method of claim 16, further wherein the both the first and the second glycosyl attachments are attached to the moiety capable of being glycosylated.

20. The method of claim 16, further wherein the second glycosyl attachment is attached to the first glycosyl attachment.

21. The method of claim 16, further wherein the first and second glycosyl transferases are the same.

22. The method of claim 16, further wherein the first and second glycosyl transferases are different.

23. The method of claim 16, further wherein the at least one second nucleotide sugar is the same as the at least one first nucleotide sugar.

24. The method of claim 16, further wherein the at least one second nucleotide sugar is different than the at least one first nucleotide sugar.

* * * * *